US007947828B2

(12) United States Patent
Yu et al.

(10) Patent No.: US 7,947,828 B2
(45) Date of Patent: May 24, 2011

(54) METHODS AND INTERMEDIATES FOR THE SYNTHESIS OF DIPYRRIN-SUBSTITUTED PORPHYRINIC MACROCYCLES

(75) Inventors: Lianhe Yu, Raleigh, NC (US); Kannan Muthukumaran, Raleigh, NC (US); Prathapan Sreedharan, Kerata (IN); Jonathan S. Lindsey, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 12/756,563

(22) Filed: Apr. 8, 2010

(65) Prior Publication Data

US 2010/0200066 A1  Aug. 12, 2010

Related U.S. Application Data

(62) Division of application No. 11/737,979, filed on Apr. 20, 2007, now Pat. No. 7,723,513, which is a division of application No. 10/456,321, filed on Jun. 6, 2003, now Pat. No. 7,332,599.

(51) Int. Cl.
*C07B 47/00* (2006.01)
*C07D 295/00* (2006.01)
(52) U.S. Cl. ............ 540/145; 548/400; 548/579
(58) Field of Classification Search .............. 540/145; 548/400, 579
See application file for complete search history.

(56) References Cited

U.S. PATENT DOCUMENTS

| | | | |
|---|---|---|---|
| 5,883,246 | A | 3/1999 | Brückner et al. |
| 5,919,923 | A | 7/1999 | Brückner et al. |
| 6,022,981 | A | 2/2000 | Brückner et al. |
| 6,407,330 | B1 | 6/2002 | Lindsey et al. |
| 6,420,648 | B1 | 7/2002 | Lindsey |
| 6,596,935 | B2 | 7/2003 | Lindsey et al. |
| 6,602,998 | B2 | 8/2003 | Kobuke et al. |
| 2003/0075216 | A1 | 4/2003 | Loewe et al. |
| 2003/0096978 | A1 | 5/2003 | Lindsey et al. |
| 2003/0096989 | A1 | 5/2003 | Lindsey et al. |

OTHER PUBLICATIONS

Li, F, et al., Design, Synthesis, and Photodynamics of Light-Harvesting Arrays Comprised of a Porphyrin and One, Two, or Eight Boron-Dipyrrin Accessory Pigments, J. Am. Chem. Soc. (1998) 10001-10013 120.
Brückner, C, et al., Synthesis of *meso*-phenyl-4,6-dipyrrins, preparation of their Cu(II), Ni(II), and Zn(II) chelates, and structural characterization of bis[*meso*-phenyl-4,6-dipyrrinato]Ni(II), Can. J. Chem. (1996) 2182-2193 74.
International Search Report for International Application No. PCT/US04/18477; Date of Mailing Mar. 31, 2005.
Li et al.; "Design, Synthesis, and Photodynamics of Light-Harvesting Arrays Comprised of a Porphyrin and One, Two, or Eight Boron-Dipyrrin Accessory Pigments" *J. Am. Chem. Soc.* 120 10001-10017 (1998).
Wagner et al., *Boron-dipyrromethene dyes for incorporation in synthetic multi-pigment light harvesting arrays*, Pure & Appl. Chem., vol. 7:1373-1380 (1996).
Brückner et al., *Synthesis of meso-phenyl-4, 6-dipyrrins, preparation of their Cu(II), Ni(II), and Zn(II) chelates, and structural characterization of bis{meso-phenyl-4, 6-dipyrrinato}Ni(II)*, Can. J. Chem, 74:2182-2193 (1996).
Brückner et al., *Synthesis, derivatization and structural characterization of octahedral tris (5-phenyl-4, 6-dipyrrinato) complexes of cobalt (III) and iron (III).*, Inorganica Chimica Acta 263:279-286 (1997).
Thompson et al., *Double-Helical Dinuclear Bis(dipyrromethene) Complexes Formed by Self-Assembly*, J. Org. Chem. 65:7870-7877 (2000).
Zhang et al., *Synthesis and Self-Assembly of a Novel Tetrapyrrole containing dipyrrin units linked at the 3,3'-positions*, Tetrahedron Letters 41:7717-7721 (2000).
Chen et al., *Synthesis and Self-Assembly of Novel Tetra- and Hexapyrroles containing dipyrrins Linked by a Sulfur Bridge at the β-position*, Tetrahedron Letters 43:8413-8416 (2002).
Yu et al., *Excited-State Energy-Transfer Dynamics in Self-Assembled Triads Composed of Two Porphyrins and an Intervening Bis(dipyrrinato) metal Complex*, Inorganic Chemistry, vol. 42, No. 21:6629-6647 (2003).
US 5,808,054, 09/1998, Brückner et al. (withdrawn)

*Primary Examiner* — Paul V. Ward
(74) *Attorney, Agent, or Firm* — Myers Bigel Sibley & Sajovec, P.A.

(57) ABSTRACT

The present invention provides dipyrrin substituted porphyrinic macrocycles, intermediates useful for making the same, and methods of making the same. Such compounds may be used for purposes including the making of molecular memory devices, solar cells and light harvesting arrays.

7 Claims, 1 Drawing Sheet

US 7,947,828 B2

METHODS AND INTERMEDIATES FOR THE SYNTHESIS OF DIPYRRIN-SUBSTITUTED PORPHYRINIC MACROCYCLES

RELATED APPLICATIONS

This application claims priority to and is a divisional U.S. patent application Ser. No. 11/737,979, filed Apr. 20, 2007, now U.S. Pat. No. 7,723,513 allowed, which is a divisional of U.S. patent application Ser. No. 10/456,321, filed Jun. 6, 2003, now U.S. Pat. No. 7,332,599, the disclosure of each which is incorporated by reference herein in its entirety.

This invention was made with government support under grant number DE-FG02-96ER14632 from the Department of Energy. The US Government has certain rights to this invention.

FIELD OF THE INVENTION

The present invention concerns methods and intermediates useful for the synthesis of dipyrrin-substituted porphyrinic macrocycles.

BACKGROUND OF THE INVENTION

The preparation of light-harvesting arrays requires the organization of a large number of pigments in well-defined 3-dimensional architectures. Porphyrinic macrocycles have been widely employed in the construction of synthetic light-harvesting arrays owing to their desirable optical and photochemical features, as well as the desire to mimic the properties of photosynthetic light-harvesting antennas (A. Burrell, et al., Chem. Rev. 101, 2751-2796 (2001)). A general limitation of porphyrins for light-harvesting purposes is that porphyrins have strong absorption only in the blue region ($\lambda_{max}$ ~420 nm), with weak absorption across the remainder of the visible spectrum. One approach to increase the spectral coverage of porphyrin-based light-harvesting arrays has been to include accessory pigments that absorb in regions where the porphyrins are relatively transparent and which funnel the resulting excited-state energy to the porphyrin. The ideal accessory pigment for use with porphyrins should have the following properties: (1) strong light absorption in the region between the porphyrin Soret and Q bands, (2) a long-lived excited-state, (3) a high level of stability, (4) synthetic compatibility with a molecular building block approach, and (5) high solubility (R. Wagner and J. Lindsey, Pure Appl. Chem., 68, 1373-1380 (1998)) Accessory pigments that have been used with porphyrins include boron-dipyrrin dyes, (R. Wagner and J. Lindsey, J. Am. Chem. Soc., 116, 9759-9760 (1994); A. Ambroise, et al., Chem. Mater., 13, 1023-1034 (2001); F. Li, et al., J. Am. Chem. Soc., 120, 10001-10017 (1998); A. Ambroise, et al. J. Org. Chem., 67, 3811-3826 (2002)), carotenoids (D. Gust, et al., Acc. Chem. Res., 34, 40-48 (2001); D. Gust, et al., Acc. Chem. Res., 16, 198-205 (1993)), coumarin dyes (S. Hecht, et al., J. Am. Chem. Soc., 123, 18-25 (2001)), cyanine dyes (Lindsey, J., et al., Tetrahedron, 45, 4845-4866 (1989)), perylene-imide dyes (A. Ambroise, et al. J. Org. Chem., 67, 3811-3826 (2002); E. Just and M. Wasielewski, Superlattices Microstr., 28, 317-328 (2000); K.-Y. Tomizaki, et al., J. Org. Chem., 67, 6519-6534 (2002)), and xanthene dyes (J. Lindsey, et al., Tetrahedron, 50, 8941-8968 (1994)). Meeting all of the criteria for an ideal accessory pigment is a significant challenge and no one class is superior in all aspects. The carotenoids absorb very strongly but have very short excited-state lifetimes, requiring very close juxtaposition for energy transfer to an acceptor. The cyanine dyes can be tuned for absorption across the visible region, but like the xanthene dyes, are positively charged, limiting solubility and typically causing difficulties in purification. The coumarins are neutral but absorb weakly and the absorption band is in the vicinity of the porphyrin Soret band, affording little additional spectral coverage. The perylene-monoimide dyes have modest absorption intensity, undergo efficient energy transfer, and are non-polar, but require extensive substitution with bulky groups to achieve adequate solubility (J. Lindsey, et al., Tetrahedron, 50, 8941-8968 (1994); R. Loewe, et al., J. Mater. Chem., 12, 3438-3451 (2002)). The boron-dipyrrin dyes have been widely used as fluorescent labels (H. Kim, et al., Chem. Commun., 1889-1890 (1999); A. Burghart, et al., J. Org. Chem., 64, 7813-7819 (1999); J. Chen, et al., J. Org. Chem., 65, 2900-2906 (2000); A. Burghart, et al., Chem. Commun., 2203-2204 (2000)) in biological applications and provide a nice compromise of all features for use with porphyrins. While the synthesis of boron-dipyrrins is more straightforward than that of perylene-imides, the one type of boron-dipyrrin that was used in conjunction with porphyrins exhibited a short, biphasic excited-state lifetime, limiting the yield of energy transfer (F. Li, et al., J. Am. Chem. Soc., 120, 10001-10017 (1998)). Accordingly, there remains a need for new types of dyes that can be used as accessory pigments with porphyrins.

SUMMARY OF THE INVENTION

A first aspect of the present invention is a method of making a bis(dipyrrinato)metal complex, comprising: reacting a dipyrromethane with an oxidant and a metal salt to produce the bis(dipyrrinato)metal complex.

A second aspect of the present invention is a method of disassembling a bis(dipyrrinato)metal complex to produce separate dipyrrin groups, comprising: reacting a bis(dipyrrinato)metal complex with a thiol reagent to disassemble the bis(dipyrrinato)metal complex into separate dipyrrin groups.

A third aspect of the present invention is a method of synthesizing a dipyrrin-substituted porphyrinic macrocycle, comprising: (a) coupling a porphyrinic macrocycle and a bis(dipyrrinato)metal complex to form a reaction product; and then (b) treating the reaction product with a thiol reagent to disassemble the reaction product and form the dipyrrin-substituted porphyrinic macrocycle.

A fourth aspect of the present invention is a method of synthesizing a dipyrrin-substituted porphyrinic macrocycle, comprising: condensing a dipyrromethane-dicarbinol with a dipyrrin-substituted dipyrromethane in a weakly polar solvent in the presence of a Lewis acid to produce a dipyrrin-substituted porphyrinic macrocycle A fifth aspect of the present invention is a method of synthesizing a trans-(dipyrrin)$_2$-porphyrinic macrocycle, comprising: reacting a dipyrrin-carboxaldehyde with a dipyrromethane in the presence of an acid catalyst to produce the trans-(dipyrrin)$_2$-porphyrinic macrocycle.

A sixth aspect of the present invention is a porphyrinic macrocycle having from 1 to 4 dipyrrin groups substituted thereon, along with polymers containing the same and substrates having such a porphyrinic macrocycle immobilized thereon or coupled thereto. In some embodiments the porphyrinic macrocycle is coupled to a substrate.

A further aspect of the present invention is a polymer comprising a plurality of linked porphyrinic macrocycles, at least one of the porphyrinic macrocycles having from 1 to 4 dipyrrins substituted thereon (e.g., a dipyrrin substituted porphyrinic macrocycle as described herein). In some embodiments such polymers are coupled to a substrate.

A further aspect of the present invention is a sandwich coordination compound, wherein at least one of the heterocyclic ligands in the sandwich coordination compound is a dipyrrin-substituted porphyrinic macrocycle as described herein. In some embodiments such compounds are coupled to a substrate.

A still further aspect of the present invention is an apparatus for storing data, said apparatus comprising a fixed electrode electrically coupled to a storage medium, said storage medium comprising a porphyrinic macrocycle having from 1 to 4 dipyrrins substituted thereon (e.g., a compound as described herein).

A still further aspect of the present invention is a light harvesting array, comprising: (a) a first substrate comprising a first electrode; and (b) a layer of light harvesting rods electrically coupled to the first electrode, each of the light harvesting rods comprising a polymer of Formula I:

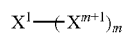
(I)

wherein: m is at least 1; $X^1$ is a charge separation group having an excited-state of energy equal to or lower than that of $X^2$; $X^2$ through $X^{m+1}$ are chromophores, and at least one of said chromophores comprises a porphyrinic macrocycle having having from 1 to 4 dipyrrins substituted thereon (e.g., a compound as described herein).

The present invention is explained in greater detail in the drawings herein and the specification set forth below.

DETAILED DESCRIPTION OF THE PREFERRED EMBODIMENTS

Figure 1:
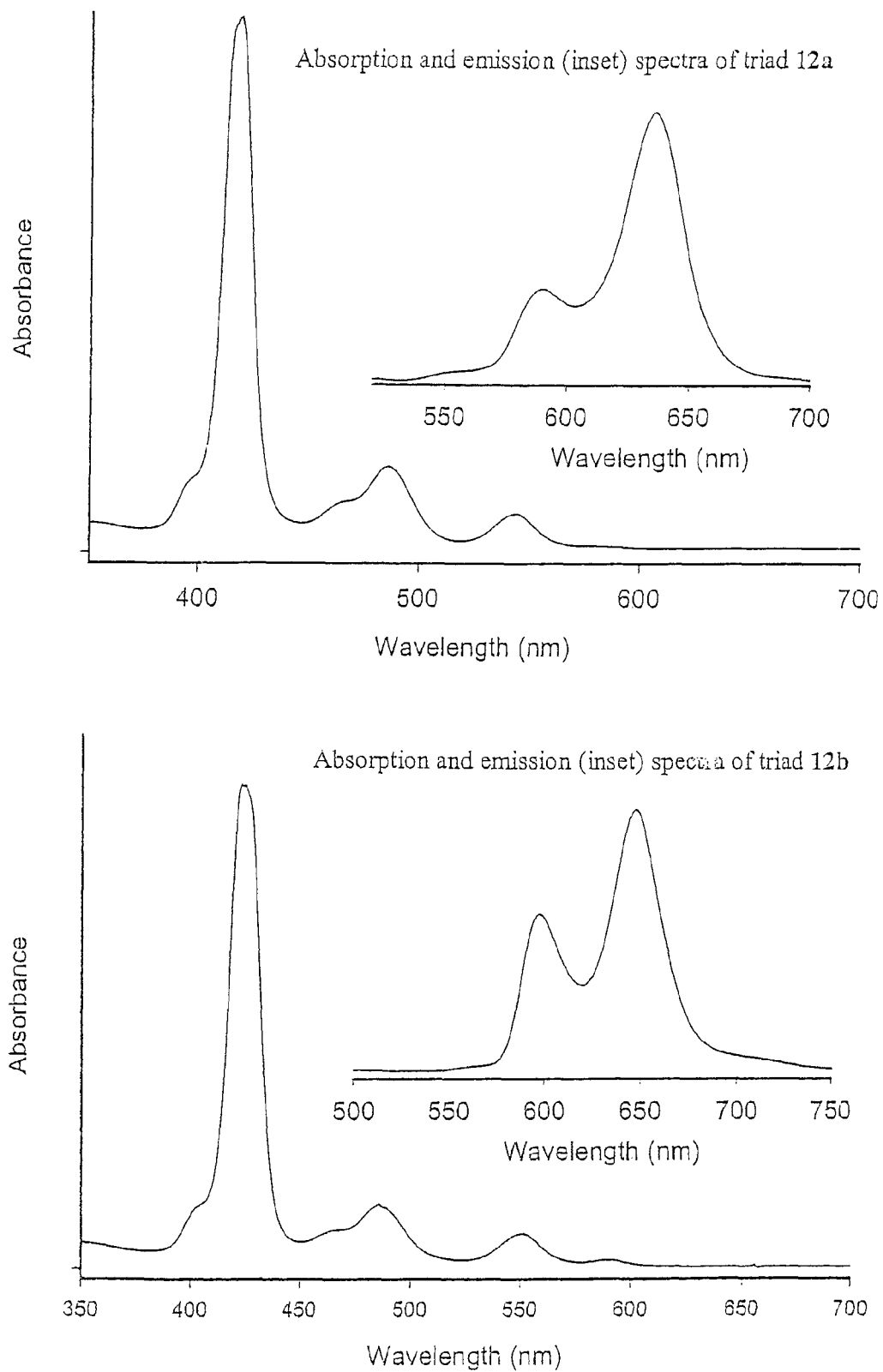
FIG. 1. Absorption and emission spectra of triads 12a and 12b in toluene at room temperature.

The term "porphyrinic macrocycle" or "porphyrin macrocycle" as used herein refers to a porphyrin or porphyrin derivative. Such derivatives include porphyrins with extra rings ortho-fused, or orthoperifused, to the porphyrin nucleus, porphyrins having a replacement of one or more carbon atoms of the porphyrin ring by an atom of another element (skeletal replacement), derivatives having a replacement of an atom of the porphyrin ring by an atom of another element (skeletal replacement), derivatives having substituents other than hydrogen located at the peripheral (meso-, β-) or core atoms of the porphyrin, derivatives with saturation of one or more bonds of the porphyrin (hydroporphyrins, e.g., chlorins, bacteriochlorins, isobacteriochlorins, decahydroporphyrins, corphins, pyrrocorphins, etc.), derivatives obtained by coordination of one or more metals to one or more porphyrin atoms (metalloporphyrins), derivatives having one or more atoms, including pyrrolic and pyrromethenyl units, inserted in the porphyrin ring (expanded porphyrins), derivatives having one or more groups removed from the porphyrin ring (contracted porphyrins, e.g., corrin, corrole) and combinations of the foregoing derivatives (e.g. phthalocyanines, porphyrazines, naphthalocyanines, subphthalocyanines, and porphyrin isomers). Preferred porphyrinic macrocycles comprise at least one 5-membered ring.

"Dipyrrin" (also known as dipyrromethene) or "dipyrrin group" as used herein includes unsubstituted or substituted dipyrrins, which may be substituted one or more times at the 1, 2, 3, 5, 7, 8 or 9 positions with any suitable substituent such as halo, carbonyl, alkyl fluoroalkyl including perfluoroalkyl, aryl (e.g., aryl at the 5 position; alkyl at the 1 and/or 9 position), fluoroaryl including perfluoroaryl, etc. Dipyrrins may be coupled to porphyrinic macrocycles at any suitable position on the dipyrrin, including the 1, 2, 3, 5, 7, 8, or 9 position.

Bis(dipyrrinato)metal and metal-dipyrrin are terms used interchangeably herein, and are sometimes symbolized as "(dp)$_2$M" or "M(dp)$_2$".

The term "alkyl," as used herein, refers to a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like, which may be substituted or unsubstituted.

The term "aryl," as used herein, refers to a monocyclic carbocyclic ring system or a bicyclic carbocyclic fused ring system having one or more aromatic rings. Representative examples of aryl include, azulenyl, indanyl, indenyl, naphthyl, phenyl, tetrahydronaphthyl, and the like, which may in turn be substituted or unsubstituted.

"Neutral conditions" as used herein refers to reaction conditions in which a Bronsted acid or an effective amount of a Bronsted acid is absent from the solvent or solvent system in which a reaction is carried out.

The terms "sandwich coordination compound" or "sandwich coordination complex" refer to a compound of the formula $L''_nM^{n-1}$, where each L is a heterocyclic ligand (as described below), each M is a metal, n is 2 or more, most preferably 2 or 3, and each metal is positioned between a pair of ligands and bonded to one or more hetero atom (and typically a plurality of hetero atoms, e.g., 2, 3, 4, 5) in each ligand (depending upon the oxidation state of the metal). Suitable metals and heterocyclic ligands include those described in U.S. Pat. No. 6,212,093 to Lindsey, incorporated herein by reference. The ligands in the sandwich coordination compound are generally arranged in a stacked orientation (i.e., are generally cofacially oriented and axially aligned with one another, although they may or may not be rotated about that axis with respect to one another). Sandwich coordination compounds may be double-decker or triple-decker sandwich coordination compounds, and may be homoleptic or heteroleptic sandwich coordination compounds.

Applicants specifically intend the disclosures of all US Patent references cited herein to be incorporated by reference herein in their entirety.

As noted above, a first aspect of the present invention is a method of making a bis(dipyrrinato)metal complex. The method may be conveniently carried out in a single step (i.e., a "single pot" or "single flask" reaction). In general, the method comprises reacting a dipyrromethane with an oxidant and a metal salt to produce said bis(dipyrrinato)metal complex. Any suitable oxidant may be employed, including but not limited to of DDQ, o-chloranil, or p-chloranil. Any suitable metal salt can be used, including but not limited to zinc, palladium, copper, nickel, or cobalt salts (though in our hands some salts did not work as noted further below). Zinc salts are currently preferred. The salts may be formed with any suitable counterion(s), including but not limited to acetate, chloride, acac (acetylacetenate), etc. The reaction temperature is not critical, and may for example be from 0 to 100° C. Room temperature is currently preferred. The reacting step may be carried out in any suitable solvent, including but not limited to dichloromethane, tetrahydrofuran, toluene, chloroform, and mixtures thereof. In general, the solvent is a non-aqueous solvent.

A second aspect of the present invention is, as also noted above, a method of disassembling a bis(dipyrrinato)metal complex to produce separate dipyrrin groups. The method generally involves reacting a bis(dipyrrinato)metal complex with a thiol reagent, preferably under neutral conditions, to disassemble the bis(dipyrrinato)metal complex into separate dipyrrin groups. Any suitable thiol reagent can be used, examples including but not limited to dithiothreitol, 2-mercaptoethanol, butanethiol, and dithioerythritol. Any suitable metal may be employed as above, including but not limited to zinc, palladium, copper, nickel or cobalt. As previously noted, the dipyrrins and in turn the bis(dipyrrinato)metal complex may be unsubstituted or substituted, and in one embodiment the complex is substituted with from 1 to 4 porphyrinic macrocycles (thus, each of the separate dipyrrin groups produced in the process in turn being dipyrrin-substituted porphyrinic macrocycles which may be used as described below). The reaction temperature is not critical and may for example be from 0 to 100° C., with room temperature currently preferred. Any of a variety of solvents may be employed, examples including but not limited to chloroform, dichloromethane, tetrahydrofuran, toluene, and mixtures thereof.

The present invention further provides a method of synthesizing a dipyrrin-substituted porphyrinic macrocycle, which method generally involves (a) coupling a porphyrinic macrocycle and a bis(dipyrrinato)metal complex to form a reaction product; and then (b) treating said reaction product with a thiol reagent to disassemble said reaction product and form said dipyrrin-substituted porphyrinic macrocycle. The coupling step may be carried out by any suitable means, such as by a Suzuki reaction or a Sonogashira reaction. For such reactions one of either the porphyrinic macrocycle and the bis(dipyrrinato)metal complex will be substituted with a first member of a reaction pair (e.g., a halogen such as fluoro, chloro, bromo, or iodo; a triflate) and the other of either the porphyrinic macrocycle and the bis(dipyrrinato)metal complex will be substituted with a corresponding second member of a reaction pair (e.g., dialkyl boronate, boronic acid or a derivative thereof; ethyne), with the members of the reaction pair selected to provide a covalent coupling between the two groups under the selected reaction conditions. Reaction conditions for Sonogashira or Suzuki couplings are well known and in general involve the presence of a palladium catalyst (non-limiting examples of which are $Pd(Oac)_2$, $Pd_2(dba)_3$, $Pd(PPh_3)_2Cl_2$, $Pd(PPh_3)_4$, etc.) and a base such as a triethylamine, diisopropylethylamine, KOH, $K_3PO_4$, $K_2CO_3$, $Na_2CO_3$, pyridine, $Ba(OH)_2$, etc. The second step (b) is a decoupling or disassembling step and is carried out as described above.

A still further aspect of the present invention is a method of synthesizing a dipyrrin-substituted porphyrinic macrocycle, comprising: condensing a dipyrromethane-dicarbinol with a dipyrrin-substituted dipyrromethane in a weakly polar solvent in the presence of a Lewis acid to produce a dipyrrin-substituted porphyrinic macrocycle. This reaction is generally carried out under conditions as described in commonly owned, copending application Ser. No. 09/962,742 (published as US-2003-0096978-A1 on May 22, 2003). In general, the reaction is carried out in a solvent having a dielectric constant of about 20, 15, or 10 or less at room temperature (e.g., 25° C.), such as hydrocarbons, chlorinated hydrocarbons, ethers, esters, glymes, tributyl borate, carbon disulfide, and mixtures thereof. Any suitable electron pair acceptor may be used as the Lewis acid, examples including but not limited to CsCl, $SmCl_3.6H_2O$, $InCl_3$, $CrF_3$, $AlF_3$, $Sc(OTf)_3$, $TiF_4$, $BEt_3$, $GeI_4$, $EuCl_3.nH_2O$, $LaCl_3$, and $Ln(OTf)_3$ where Ln=lanthanide. The concentration thereof may range, for example, from 0.001 or 0.01 nmol/L to 100 or 500 mmol/L, or more. As above, the dipyrromethane-dicarbinol may have at least one porphyrinic macrocycle covalently coupled thereto, which porphyrinic macrocycle may be metalated, with the condensing step being carried out without demetalation of the porphyrinic macrocycle.

A further aspect of the present invention is a method of synthesizing a trans-(dipyrrin)$_2$-porphyrinic macrocycle, comprising: reacting a dipyrrin-carboxaldehyde with a dipyrromethane in the presence of an acid catalyst to produce said trans-(dipyrrin)$_2$-porphyrinic macrocycle. Any suitable acid catalyst may be used, including but not limited to trifluoroacetic acid, $BF_3.O(Et)_2$ and $NH_4Cl$, trichloroacetic acid, etc.). The reacting step may be carried out at any suitable temperature, such as from 0 to 100° C. (preferably room temperature), and in any suitable solvent, examples including but not limited to dichloromethane, tetrahydrofuran, toluene, acetonitrile, chloroform, and mixtures thereof.

The methods and intermediates described herein may be used to produce a porphyrinic macrocycle having from 1 to 4 dipyrrin groups substituted thereon. As indicated above, the dipyrrins are preferably substituted on the porphyrinic macrocycle at the meso and/or beta positions of the porphyrinic macrocycle, and the dipyrrins are preferably coupled at or by the 1, 2, 3, 5, 7, 8 or 9 position of the dipyrrin. In one preferred embodiment, the porphyrinic macrocycle has two dipyrrins trans substituted thereon (and may optionally include additional dipyrrins substituted at additional locations thereon).

The dipyrrin-substituted porphyrinic macrocycles of the present invention are useful, among other things, for the production of polymers thereof which may be immobilized or coupled to a substrate and used as light harvesting rods, light harvesting arrays, and solar cells, as described for example in U.S. Pat. No. 6,407,330 to Lindsey et al. or U.S. Pat. No. 6,420,648 to Lindsey. For example, a light harvesting rod or a solar cell which may be produced with compounds of the present invention may comprise: (a) a first substrate comprising a first electrode; (b) in the solar cell a second substrate comprising a second electrode, with the first and second substrate being positioned to form a space therebetween, and with at least one of (i) the first substrate and the first electrode and (ii) the second substrate and the second electrode being transparent; and (c) a layer of light harvesting rods electrically coupled to the first electrode, each of the light harvesting rods comprising a polymer of Formula I:

(I)

wherein: m is at least 1 (and typically two, three or four to twenty or more); $X^1$ is a charge separation group having an excited-state of energy equal to or lower than that of $X^2$; $X^2$ through $X^{m+1}$ are chromophores (each of which may be a compound produced by the methods of the present invention); and $X^1$ is electrically coupled to the first electrode; and (d) preferably, an electrolyte in the space between the first and second substrates. A mobile charge carrier can optionally be included in the electrolyte.

Dipyrrin-substituted porphyrinic macrocycles are also useful immobilized to a substrate for making charge storage molecules and information storage devices containing the same. Such charge storage molecules and information storage devices are known and described in, for example, U.S. Pat. No. 6,208,553 to Gyko et al.; U.S. Pat. No 6,381,169 to Bocian et al.; and U.S. Pat. No 6,324,091 to Gryko et al. The dipyrrin-substituted porphyrinic macrocycle may be comprise a member of a sandwich coordination compound in the information storage molecule, such as described in U.S. Pat. No. 6,212,093 to Li et al. or U.S. Pat. No. 6,451,942 to Li et al.

The present invention is explained in greater detail in the Examples set forth below.

EXPERIMENTAL

Dipyrrins provide the basis for the boron-dipyrrin dyes (A. Treibs and F.-H. Kreuzer, *Liebigs Ann. Chem.*, 718, 208-223 (1968)) but also have a rich chemistry with diverse transition metals. Free base dipyrrins react readily with a wide variety of metal salts, affording the corresponding bis(dipyrrinato)metal(II) or tris(dipyrrinato)metal(III) complexes. Such complexes typically absorb quite strongly in the blue-green region ($\lambda_{max}$~470-500 nm; $\in_{\lambda max}$ 50,000-100,000 $M^{-1}$ $cm^{-1}$). However, the photochemical properties of bis(dipyrrinato)metal complexes have rarely been studied. The bis(dipyrrinato) metal complexes derived from a divalent metal such as zinc are fundamentally distinct from the dipyrrinatoboron difluoride complexes (Chart 1); the latter comprise only one dipyrrin ligand per boron and typically are quite fluorescent.

Chart 1

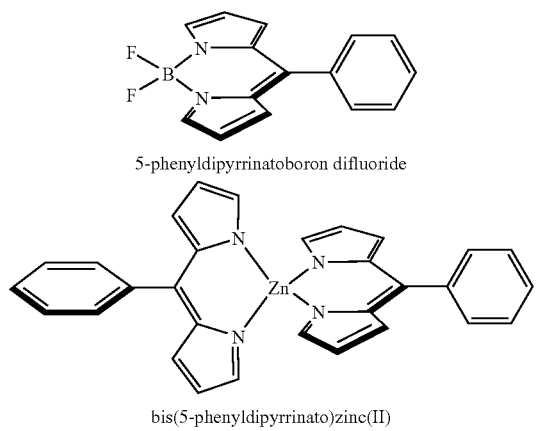

5-phenyldipyrrinatoboron difluoride bis(5-phenyldipyrrinato)zinc(II)

The chemistry of bis(dipyrrinato)metal complexes dates to the time of Fischer, where dipyrrins (previously termed pyrromethenes or dipyrromethenes) (G. Moss, *Pure Appl. Chem.*, 59, 779-832 (1987)) employed as precursors to naturally occurring porphyrins were found to form stable complexes with metals such as iron, copper, cobalt, nickel, and zinc (H. Fischer and M. Schubert, *Ber.*, 57, 610-617 (1924); H. Fischer and J. Klarer, *Ann.*, 448, 178-193 (1926)). The dipyrrins, obtained by oxidation of dipyrromethanes, typically contained a full complement of substituents at the α-and β-positions of the chromophore. In the ensuing years, complexes of diverse divalent metals (Mg, Ca, Mn, Fe, Co, Ni, Cu, Zn, Pd, Cd, Hg)(A. Corwin and M. Melville, *J. Am. Chem. Soc.*, 77, 2755-2759 (1955); R. Motekaitis and A. Martell, *Inorg. Chem.*, 9, 1832-1839 (1970); A. Corwin and V. L. Sydow, *J. Am. Chem. Soc.*, 75, 4484-4486 (1953); C. Porter, *J. Chem. Soc.*, 368-372 (1938); J. Fergusson and C. Ramsay, *J. Chem. Soc.*, 5222-5225 (1965); Y. Murakami and K. Sakata, *Inorg. Chim. Acta*, 273-279 (1968); Y. Murakami, et al., *Inorg. Chim. Acta*, 671-675 (1969); F. March, et al., *J. Chem. Soc.*, 440-448 (1971); Y. Murakami, et al., *Inorg. Chem.*, 10, 1728-1734 (1971); Y. Murakami, et al., *J. Chem. Soc., Dalton Trans.*, 1729-1734 (1973); Y. Murakami, et al., *J. Chem. Soc., Dalton Trans.*, 1734-1737 (1973); A. Johnson, et al., *J. Chem. Soc.*, 3416-3424 (1959)) have been prepared from similarly substituted dipyrrins.

In the past decade, dipyrromethanes that bear one meso-substituent and lack any α-or β-substituents have become available via a simple one-flask synthesis (C.-H. Lee and J. Lindsey, *Tetrahedron*, 50, 11427-11440 (1994); B. Littler, et al., *J. Org. Chem.*, 64, 1391-1396 (1999)). Dolphin's group (C. Brückner, et al., *Can. J. Chem.*, 74, 2182-2193 (1996)) found that exposure of such meso-substituted dipyrromethanes to DDQ or p-chloranil afforded the corresponding dipyrrins. Dolphin also showed that such dipyrrins could be converted to the corresponding bis(dipyrrinato)metal complex (C. Brückner, et al., *Can. J. Chem.*, 74, 2182-2193 (1996)) [M(dp)$_2$] or tris(dipyrrinato)metal complex (C. Brückner, et al., *Inorg. Chim. Acta*, 263, 279-286 (1997)) upon treatment with base and a divalent (M=Zn, Cu, Ni) or trivalent (Co, Fe) metal acetate. Dolphin subsequently showed that a variety of elegant structures could self-assemble from multimers of the basic dipyrrin motif (Y. Zhang, et al., *J. Am. Chem. Soc.*, 120, 13537-13538 (1998); A. Thompson, et al., *Chem. Commun.*, 631-632 (1999); A. Thompson and D. Dolphin, *J. Org. Chem.*, 65, 7870-7877 (2000); A. Thompson and D. Dolphin, *Org. Lett.*, 2, 1315-1318 (2000)). Similar structures have been made by others (Y. Zhang and J. Ma, *Org. Prep. Proc. Mt.*, 33, 81-86 (2001); Y. Zhang, et al., *Tetrahedron Lett.*, 41, 7717-7721 (2000)). The ready access to dipyrromethanes/dipyrrins and the facile self-assembly of bis(dipyrrinato)metal complexes prompted us to consider the use of this motif as the basis for linking porphyrins in a self-assembly process. Given the strong absorption in the green region, we also sought to examine whether excited-state energy transfer would occur from the bis(dipyrrinato) metal unit to the attached porphyrin. Such a process, if viable, would afford a self-assembling accessory pigment for elaborating multiporphyrin light-harvesting arrays. This approach closely resembles the strategy employed by the groups of Collin, Flamigni, and Sauvage where a terpyridine-porphyrin reacts with a ruthenium (or iridium) reagent to give the array containing two porphyrins joined by a bridging bis(terpyridyl)ruthenium (or iridium) complex (L. Flamigni, et al., *Coord. Chem. Rev.*, 190-192, 671-682 (1999); A. Harriman and J.-P. Sauvage, *Chem. Soc. Rev.*, 25, 41-48 (1996); L. Flamigni, et al., *Chem. Eur. J.*, 4, 1744-1754 (1998); I. Dixon, et al., *Inorg. Chem.*, 40, 5507-5517 (2001); L. Flamigni, et al., *J. Phys. Chem. B*, 106, 6663-6671 (2002)). More generally, the self-assembly approach is inspired by a rich collection of self-assembled arrays comprised of porphyrins and metal-coordinated ligands (J.-C. Chambron, et al., In *The Porphyrin Handbook*; Kadish, K. M.; Smith, K. M.; Guilard, R., Eds.; Academic Press: San Diego, Calif. 2000, Vol. 6, pp 1-42; T. Imamura and K. Fukushima, *Coord. Chem. Rev.*, 198, 133-156 (2000); J. Wojaczynski and L. Latos-Grazynski, *Coord. Chem. Rev.*, 204, 113-171 (2000)).

We here describe the synthesis of a number of metal-dipyrrin complexes. We then investigate three routes for forming porphyrin-dipyrrins. The porphyrin-dipyrrins are used to create triads consisting of two zinc porphyrins joined by an intervening metal-dipyrrin complex. The spectroscopic properties of several Zn-dipyrrin complexes as well as the all-Zn triads have been characterized. This work provides the foundation for the use of metal-dipyrrin complexes as self-assembling chromophores in light-harvesting systems and self-assembling linkers in molecular information storage devices.

Results and Discussion

I. Synthesis

A. Preparation of 5-substituted dipyrromethanes. Dipyrromethanes bearing various substituents at the 5-position are readily available via condensation of the corresponding aldehyde+pyrrole under TFA catalysis (C.-H. Lee and J. Lindsey, Tetrahedron, 50, 11427-11440 (1994); B. Littler, et al., J. Org. Chem., 64, 1391-1396 (1999)). The dipyrromethanes 1a-j were prepared as shown in Scheme 1.

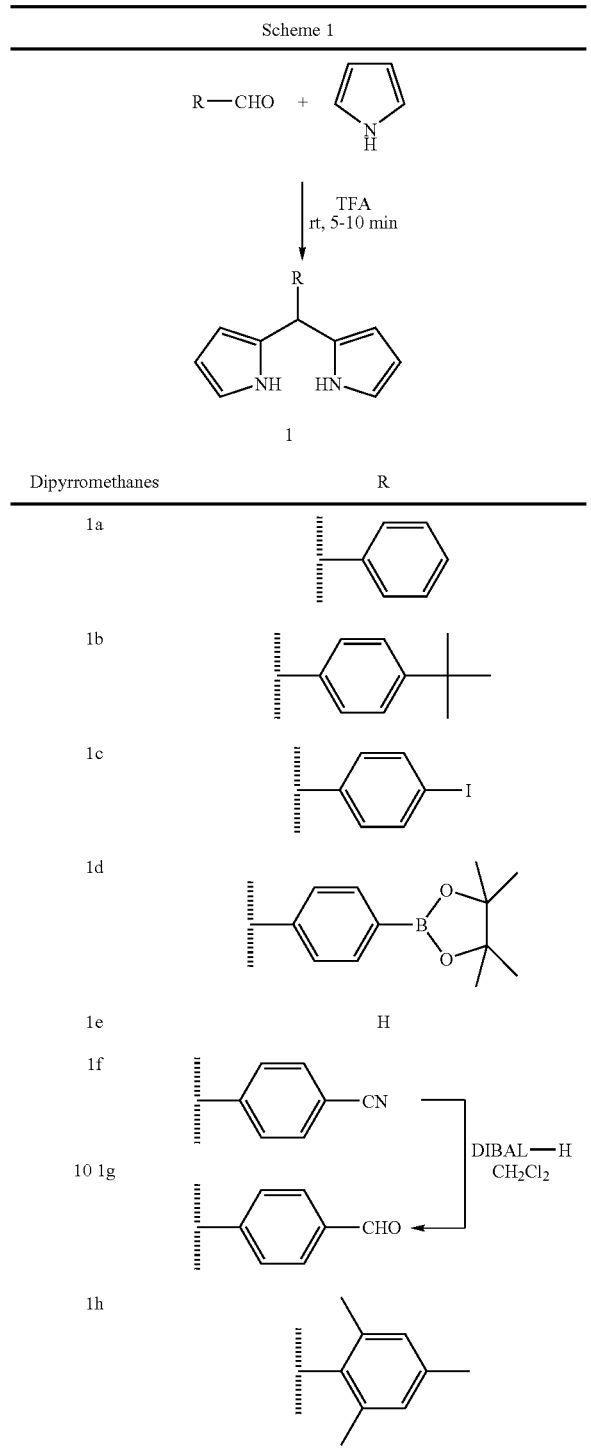

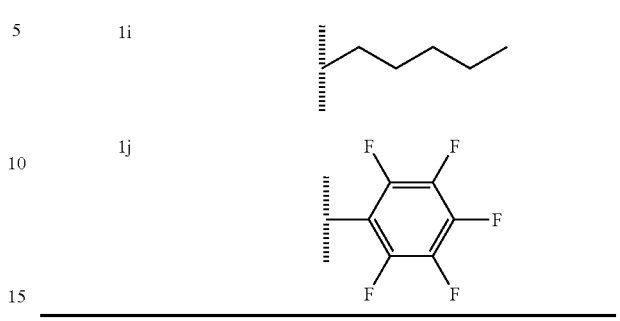

B. Preparation of free base dipyrrins and metal-dipyrrin complexes. Brückner et al. reported that oxidation of 5-phenyldipyrromethane (1a) with DDQ in benzene at room temperature affords 5-phenyldipyrrin (2a) in 47% yield (C. Brückner, et al., Can. J. Chem., 74, 2182-2193 (1996)). We performed the same reaction in THF, a solvent providing much higher solubility for quinones than benzene (D. Walker and J. Hiebert, Chem. Rev., 67, 153-195 (1967)). The reaction with DDQ for 40 min gave 2a in 42% yield, while the milder oxidant p-chloranil for 18 h gave 2a in 62% yield. Similarly, oxidation of 1b, 1h, and 1j with DDQ in THF afforded the corresponding free base dipyrrins 2b, 2h and 2j in 51%, 57% and 85% yield, respectively.

Brückner et al. reported two approaches for the formation of dipyrrinato-metal complexes: (1) the traditional treatment of a purified dipyrrin with a metal acetate (C. Brückner, et al., Can. J. Chem., 74, 2182-2193 (1996)), or (2) a two-step one-flask approach involving oxidation of a dipyrromethane yielding the dipyrrin followed by treatment of the crude dipyrrin with TEA and a metal acetate (C. Brückner, et al., Inorg. Chim. Acta, 263, 279-286 (1997)). Application of the first approach with 2b and $Cu(OAc)_2 \cdot H_2O$ in $CH_2Cl_2$/MeOH at room temperature for 10 min afforded the bis(dipyrrinato) copper(II) species Cu-2b in 82% yield (42% from 1b) after chromatographic purification. Similar attempts to metalate 2b using either $Pd(OAc)_2$ or $Pd(NO_3)_2$ in different solvents over a range of temperatures gave either a low yield (10%) or complicated product distributions. However, exposure of 2b to $Pd_2(dba)_3$ in $CHCl_3$/MeOH/TEA at room temperature afforded the Pd-2b after a simple chromatographic purification (Scheme 2). The overall yield from dipyrromethane 1b was 43%.

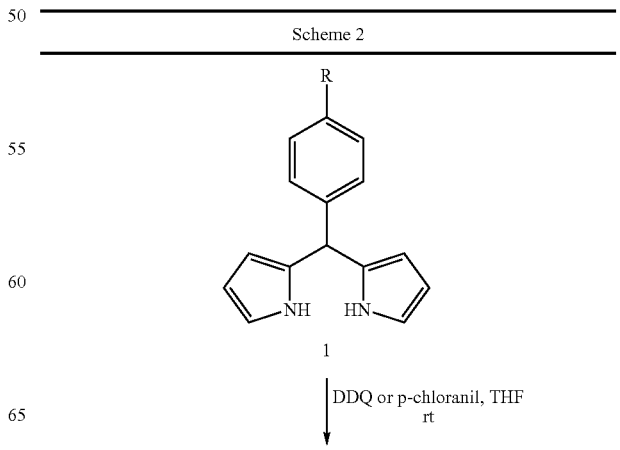

Scheme 2

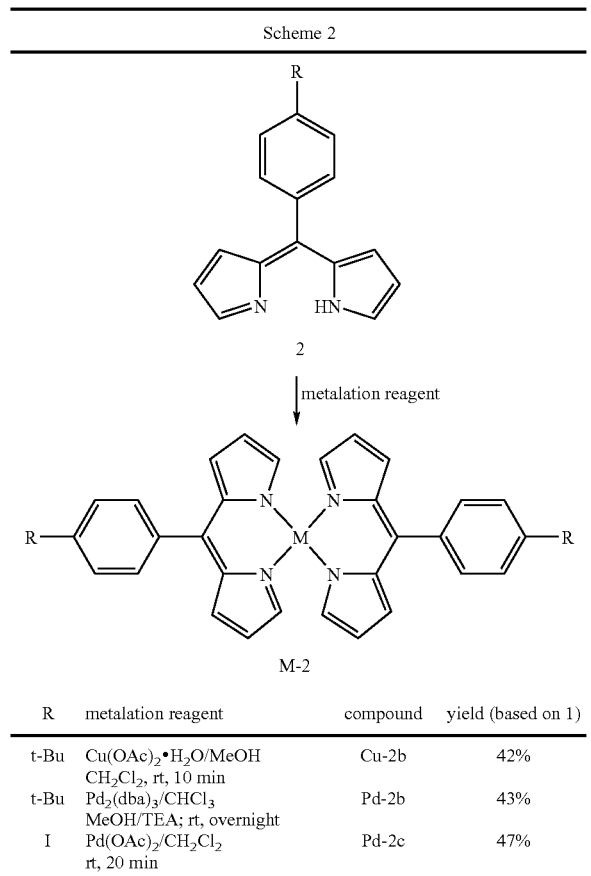

| R | metalation reagent | compound | yield (based on 1) |
|---|---|---|---|
| t-Bu | Cu(OAc)$_2$•H$_2$O/MeOH CH$_2$Cl$_2$, rt, 10 min | Cu-2b | 42% |
| t-Bu | Pd$_2$(dba)$_3$/CHCl$_3$ MeOH/TEA; rt, overnight | Pd-2b | 43% |
| I | Pd(OAc)$_2$/CH$_2$Cl$_2$ rt, 20 min | Pd-2c | 47% |

Similar attempts to prepare the desired bis[(4-iodophenyl)dipyrrinato]palladium(II) complex Pd-2c by using Pd$_2$(dba)$_3$ were not successful. In a two-step approach, dipyrromethane 1c was treated with p-chloranil, the crude reaction mixture was filtered to remove quinone species, and the crude dipyrrin was treated with Pd(OAc)$_2$ in CH$_2$Cl$_2$ to give Pd-2c in 43% overall yield after simple filtration (Scheme 2). It is noteworthy that this method did not involve any chromatographic processes.

C. One-flask synthesis of bis(dipyrrinato)zinc(II) complexes. The facile formation of bis(dipyrrinato)zinc(II) complexes prompted us to investigate a one-flask synthesis. Thus, treatment of 5-phenyldipyrromethane (1a) with an equimolar amount of DDQ in THF for 30 min at room temperature in the presence of Zn(OAc)$_2$.2H$_2$O afforded bis(5-phenyldipyrrinato)zinc(II) (Zn-2a) in 78% yield after column chromatography (Scheme 3). With the milder oxidant p-chloranil in place of DDQ, the oxidation/complexation of 1a was complete in ~27 h, but gave a cleaner reaction than that with DDQ. The product was obtained in 81% yield after column chromatography. Under the same conditions, Zn-2b, Zn-2c, Zn-2d, Zn-2g, and Zn-2h were prepared in good yield. The same reaction of 1e (no meso-substituent) or 1i (containing a meso-alkyl substituent) with DDQ or p-chloranil failed to give the desired bis(dipyrrinato)zinc(II) complexes, though in both cases the starting material (dipyrromethane) was completely consumed. The failure must originate in the oxidation rather than the complexation process, because in each case, oxidation (DDQ or p-chloranil) alone failed to afford the expected free base dipyrrin.

Scheme 3

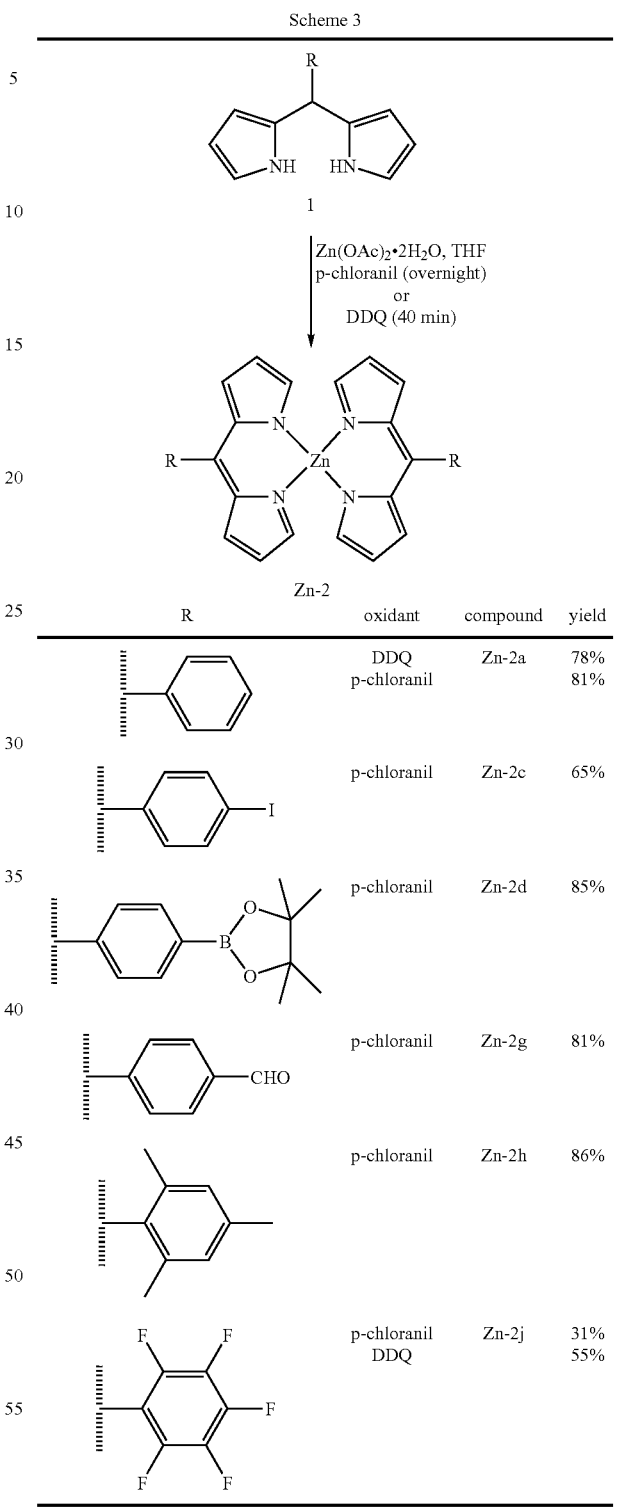

The attempted metalation of 5-phenyldipyrrin (1a) with CaCl$_2$, MgBr$_2$.OEt$_2$ or Cd(OAc)$_2$.2H$_2$O was not successful as evidenced by UV-Vis and $^1$H NMR spectroscopic analysis of the crude reaction mixture. The failure in these cases was surprising, because each type of complex has been prepared from dipyrrins with a full complement of α-and β-substituents. The conditions for MgBr$_2$.OEt$_2$ were very similar to those used for magnesiation of porphyrins (J. Lindsey and J.

Woodford, *Inorg. Chem.*, 34, 1063-1069 (1995)). Failure of these metals (Ca, Mg, Cd) in the one step process implies failure in the one flask process.

D. Demetalation of metal-dipyrrin complexes. We investigated methods for the demetalation of bis(dipyrrinato)metal complexes because we wanted to be able to (1) disassemble self-assembled structures, and (2) remove metals employed for protective purposes during specific synthetic transformations (vide infra). We first examined the acid-induced demetalation of Zn-2a to give 5-phenyldipyrrin (2a). However, only partial demetalation was observed with use of excess TFA (50 equiv) in $CH_2Cl_2$ for several hours. Even use of methanolic HCl did not afford complete demetalation. Because the dipyrrin-metal complexes were resistant to acid hydrolysis, an alternative method of demetalation was explored.

Dithiothreitol (threo-1,4-dimercapto-2,3-butanediol, DTT) is a non-volatile, thiol-containing ligand capable of coordinating with a variety of metal ions. We examined the use of DTT to liberate the free base dipyrrins by displacement of the metal from the complexes (Scheme 4). Treatment of Cu-2b in $CH_2Cl_2$ (5 mM) with 10 molar equivalents of DTT at room temperature gave quantitative demetalation as observed by TLC and UV-vis spectroscopic analysis. The free base dipyrrin 2b was obtained in 95% yield after chromatographic purification. Each zinc(II)-dipyrrin complex that was examined also was readily demetalated under the same conditions within 30 min (Scheme 4). The palladium(II)-dipyrrin complexes Pd-2b and Pd-2c demetalated much more slowly (17 h) under the same conditions, yet the free base dipyrrins 2b and 2c were obtained in 79% or 89% yield (Scheme 4). It is noteworthy that treatment of Zn-1a with ethylene glycol in place of DTT caused no demetalation, indicating that the thiols of DTT are important for the demetalation process.

Scheme 4

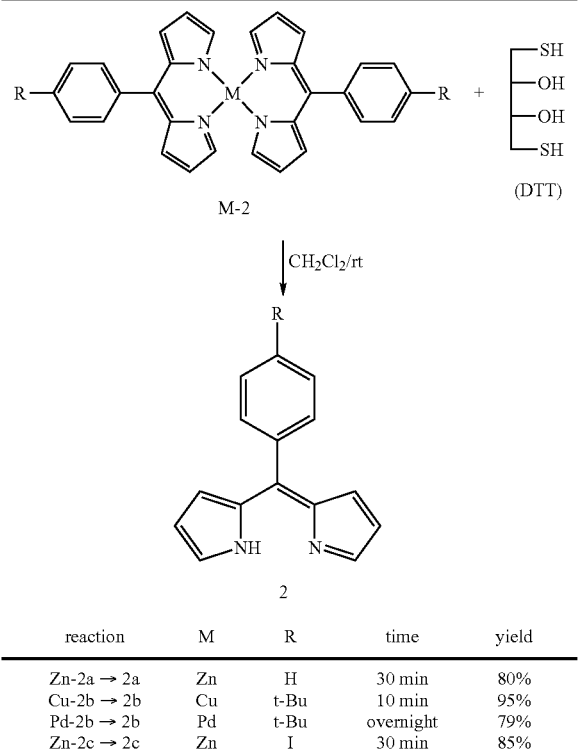

| reaction | M | R | time | yield |
|---|---|---|---|---|
| Zn-2a → 2a | Zn | H | 30 min | 80% |
| Cu-2b → 2b | Cu | t-Bu | 10 min | 95% |
| Pd-2b → 2b | Pd | t-Bu | overnight | 79% |
| Zn-2c → 2c | Zn | I | 30 min | 85% |
| Pd-2c → 2c | Pd | I | overnight | 89% |
| Zn-2g → 2g | Zn | CHO | 60 min | 31% |

We examined an alternative method for removing the metal from the $M(dp)_2$ complexes. Treatment of Cu-2b with $NaBH_4$ (20 molar equivalents) in THF/MeOH (3:1) at room temperature for 20 min gave complete reduction, affording dipyrromethane 1b in 88% yield after chromatographic purification. However, Zn-2a gave only a 50% yield of 1a upon similar reduction. Dipyrrins are well known to undergo reduction to give the dipyrromethane (A. Gossauer and J. Engel, In *The Porphyrins*; Dolphin, D. Ed., Academic Press: New York, 1978, Vol. II, pp 197-253). Indeed, Dolphin showed that meso-substituted dipyrrins could be converted to the dipyrromethanes upon reduction with $NaBH_4$ (C. Brückner, et al., *Can. J. Chem.*, 74, 2182-2193 (1996)). Our results show that the reduction can be performed with dipyrrins in the metal complexes.

E. Routes to porphyrin-dipyrrins. We developed three routes for the synthesis of porphyrin-dipyrrin systems. The first two routes employ a porphyrin building block, while the third route employs a dipyrrin in a porphyrin-forming reaction.

Route 1: Suzuki coupling of a porphyrin and a bis(dipyrrinato)metal complex. The synthesis of the key porphyrin building block for use in a Suzuki coupling reaction is shown in Scheme 5. Treatment of dipyrromethane 1e and mesitaldehyde with $BF_3$-ethanol cocatalysis ($BF_3.OEt_2$ in $CHCl_3$ containing 0.75% ethanol) (J. Lindsey and R. Wagner, *J. Org. Chem.*, 54, 828-836 (1989)) for 0.5 h at room temperature followed by oxidation with DDQ afforded the desired porphyrin. No acidolytic scrambling leading to undesired porphyrin products was detected as evidenced by LD-MS analysis of the crude reaction mixture. Chromatographic purification gave the desired porphyrin 3 in 28% yield. Following a standard procedure (L. Nudy, et al., *Tetrahedron*, 40, 2359-2363 (1984); S. DiMagno, et al, *J. Org. Chem.*, 58, 5983-5993 (1993)), mono-bromination was carried out by treatment of 5,15-dimesitylporphyrin (3) with 1 molar equivalent of NBS in $CHCl_3$/pyridine for 25 min at 0° C. The dibrominated byproduct was easily separated by column chromatography. The desired product 4 was obtained in 72% yield, accompanied by the dibrominated byproduct (12% yield) and the unreacted starting porphyrin 3 (12%). No β-bromination was observed by $^1H$ NMR spectroscopic analysis. Metalation of 4 with $Zn(OAc)_2.2H_2O$ afforded Zn-4 in 98% yield. Following the conditions used previously for Suzuki coupling at the porphyrin meso-positions (A. Hyslop, et al., *J. Am. Chem. Soc.*, 120, 12676-12677 (1998); M. Murata, et al., *J. Org. Chem.*, 62, 6458-6459 (1997)), reaction of Zn-4 and 4,4,5,5-tetramethyl-1,3,2-dioxaborolane in the presence of TEA/Pd$(PPh_3)_2Cl_2$ in 1,2-dichloroethane at 85° C. for 1 h afforded the desired product Zn-5 in 93% yield after column chromatography.

Scheme 5

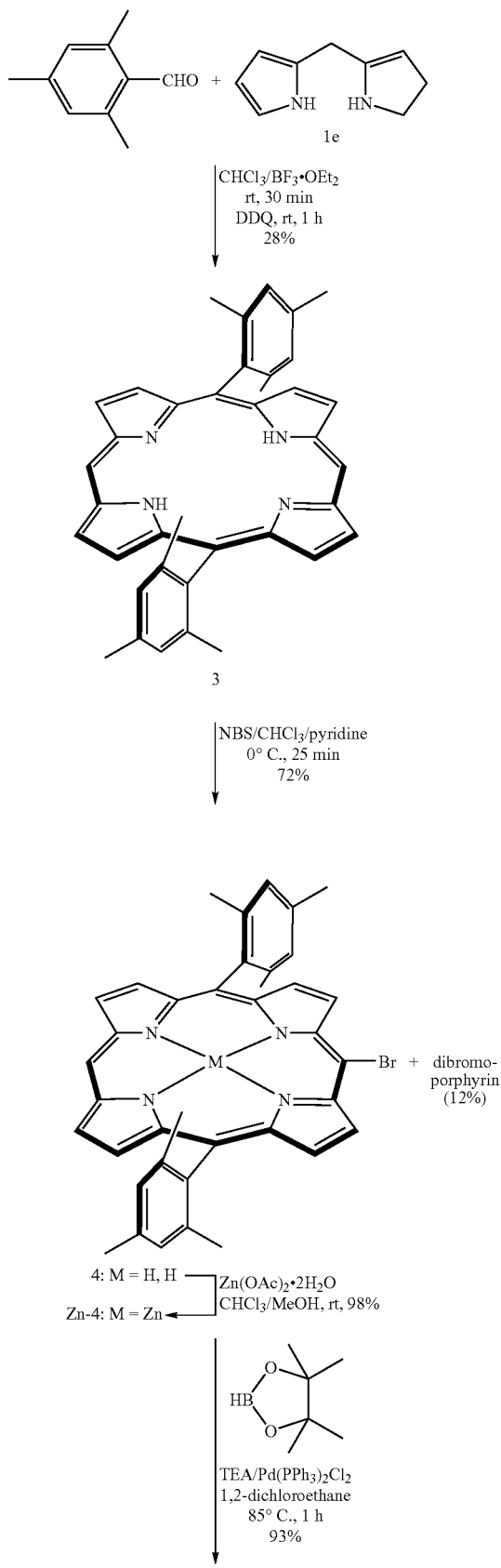

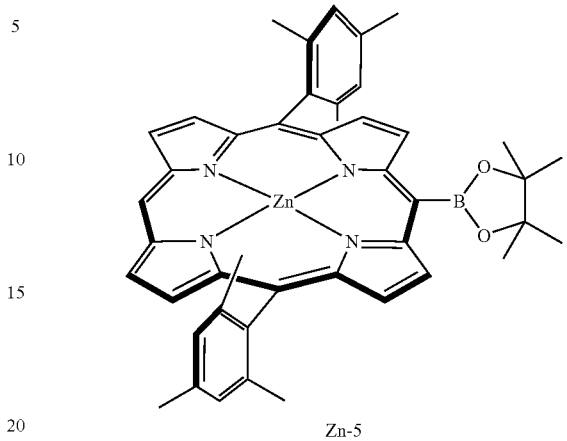

Zn-5

A number of approaches were explored for the Suzuki coupling of a porphyrin and a dipyrrin species. Attempts to couple boronate-porphyrin Zn-5 and iodo-complex Zn-2c, or bromo-porphyrin Zn-4 and boronate-complex Zn-2d, under standard Suzuki coupling conditions resulted in failure, which we attributed to the sequestration of palladium by the dipyrrins following transmetalation of zinc. A large number of control experiments showed that Suzuki reactions are poisoned by the presence of a free base dipyrrin, bis(dipyrrinato)zinc(II), or bis(dipyrrinato)copper(II), even if the dipyrrin has no functional groups to participate as a coupling partner. We turned to the use of Pd-2c for the Suzuki reaction.

Reaction of Zn-5 and Pd-2c under the conditions employed previously (L. Yu and J. Lindsey, *Tetrahedron*, 57, 9285-9298 (2001)) gave the $(ZnP-dp)_2Pd$ triad 6 in only 6% yield (where ZnP indicates the zinc porphyrin). We examined the Suzuki coupling of Zn-5 and Pd-2c under conditions similar to those employed by Therien et al. for attachment of substituents to the porphyrin meso-position (P. Iovine, et al., *J. Am. Chem. Soc.*, 112, 8717-8727 (2000)): $Pd[(PPh_3)]_4$ (15% mol relative to Zn-5); $Ba(OH)_2 \cdot 8H_2O$ (1 equiv relative to Zn-5), DME/$H_2O$ (10:1) at 80° C. under argon, the concentration of [Zn-5]=20 mM and [Pd-2c]=10 mM. TLC analysis showed complete consumption of the starting porphyrin after 2 h. Analytical size exclusion chromatography (SEC) indicated the desired triad was formed in ~50% yield, and a considerable amount of monomeric porphyrin species was present (~45%, as indicated by analytical SEC). LD-MS analysis of this product showed that deboronation and phenylation is the major side reaction in this Suzuki coupling. Purification by silica gel chromatography, preparative SEC and silica gel chromatography afforded the desired $(ZnP-dp)_2Pd$ triad in 50% yield (Scheme 6).

Scheme 6
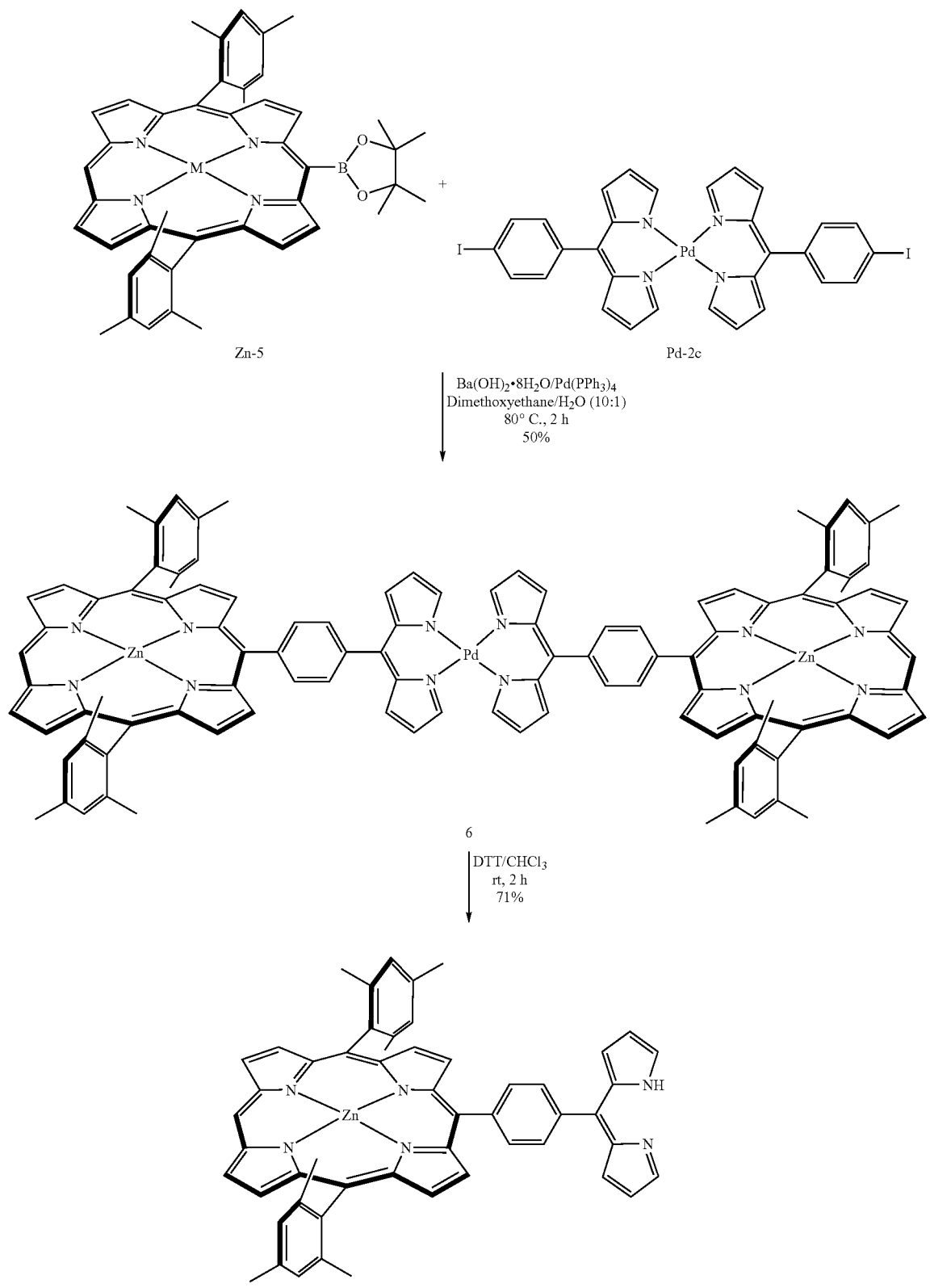

Treatment of 6 with DTT at room temperature resulted in selective demetalation of the Pd-dipyrrin complex, affording the porphyrin-dipyrrin 7a in 71% yield. No demetalation of the Zn-porphyrin was observed by UV-Vis absorption or LD-MS analysis.

Route 2: Formation and oxidation of a dipyrromethane-substituted porphyrin. The second route entails the synthesis of a porphyrin-dipyrromethane, which is then oxidized to the porphyrin-dipyrrin. The reaction of bromo-porphyrin 4 and 4-formylphenyl boronic acid under standard Suzuki coupling conditions afforded porphyrin 8a in 90% yield (Scheme 7). Porphyrin-benzaldehyde 8b was prepared via the reaction of a dipyrromethane bearing a carboxaldehyde group and a dipyrromethane-dicarbinol (L. Yu and J. Lindsey, Tetrahedron, 57, 9285-9298 (2001)).

equiv of TFA was employed, only a tiny amount of porphyrin-dipyrromethane was formed as evidenced by TLC and LD-MS analysis. Increasing the amount of TFA to 1.1 equiv led to complete consumption of the porphyrin-benzaldehyde in 2 h. The product was isolated in >80% yield by chromatographic purification [silica, CHCl$_3$/TEA (99:1)]. An eluant containing 1% TEA was employed during purification via silica column chromatography given the lability of dipyrromethanes toward weak acidic conditions. When the condensation was performed in the presence of 1.5 equiv of TFA, the porphyrin-benzaldehyde was completely consumed after 30 min at room temperature. The isolated yield was similar to that when 1.1 equiv of TFA was used. Under such conditions, porphyrin-dipyrromethanes 9a and 9b were prepared in good yield (Scheme 8).

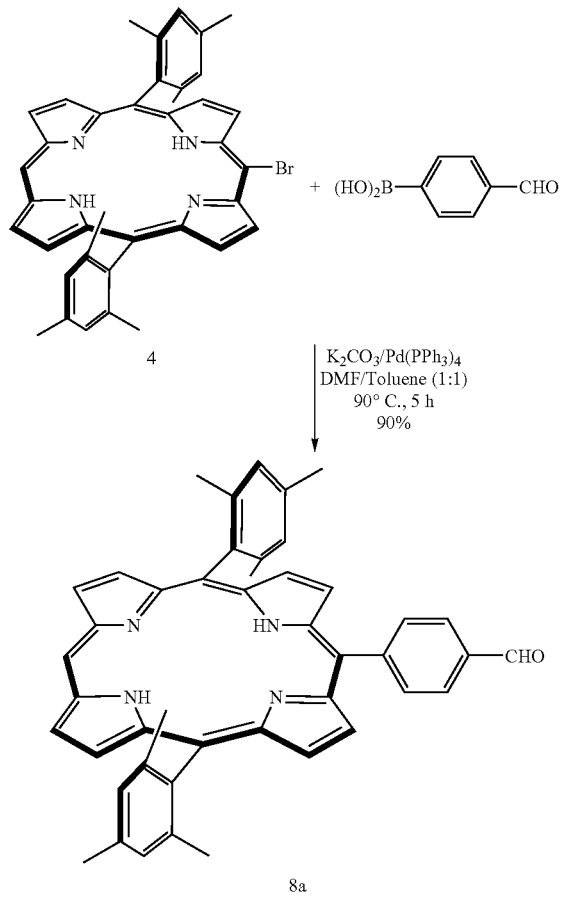

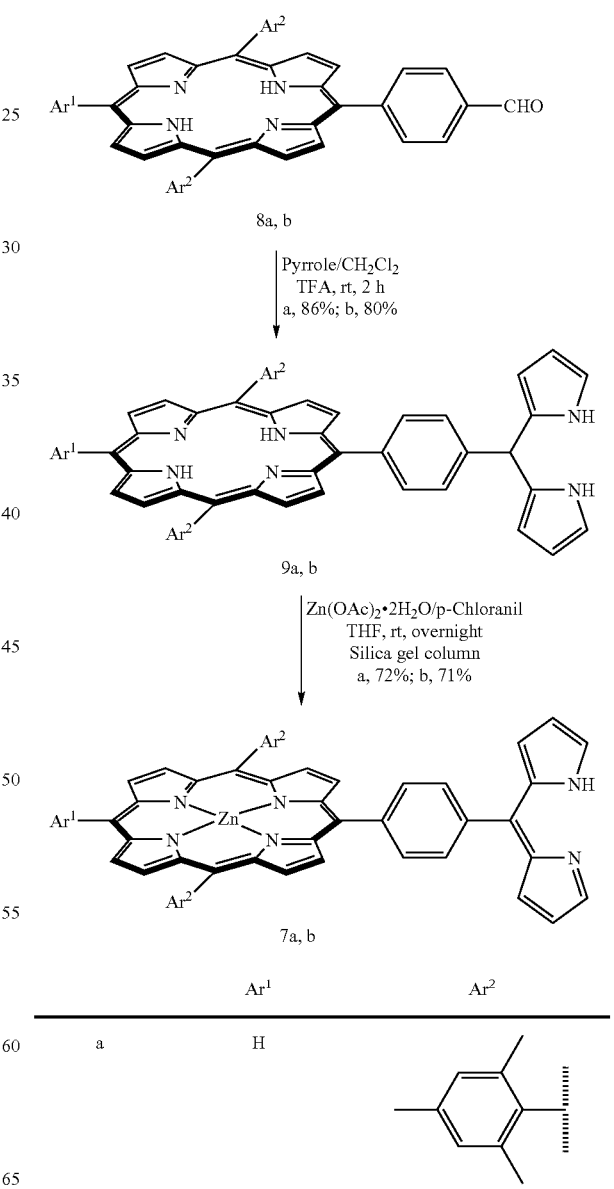

The availability of porphyrin-benzaldehydes prompted us to explore the conditions for preparing the porphyrin-substituted dipyrromethanes, following the general method for preparing dipyrromethanes shown in Scheme 1. In this method, the aldehyde is dissolved in neat pyrrole and then treated with a catalytic amount of TFA at room temperature (C.-H. Lee and J. Lindsey, Tetrahedron, 50, 11427-11440 (1994); B. Littler, et al., J. Org. Chem., 64, 1391-1396 (1999)). We modified this method slightly (R. Loewe, et al., J. Mater. Chem., 12, 3438-3451 (2002); M. Speckbacher, et al., Inorg. Chem., in press (2003)). A solution of porphyrin-benzaldehyde (~15 mM) in dichloromethane was treated with a large excess of pyrrole (300-400 molar equivalents). When 0.1

Scheme 8

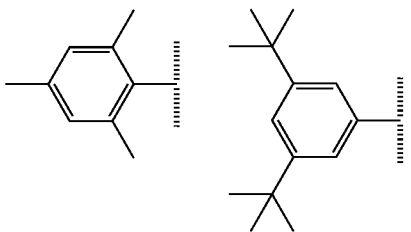

The porphyrin-dipyrromethanes were treated under the conditions for dipyrrin formation, employing p-chloranil in the presence of Zn(OAc)$_2$·2H$_2$O. The presumed product in this reaction is the triad composed of two Zn porphyrins attached to a central zinc-dipyrrin complex. However, such triads are not stable upon exposure to the silica chromatographic purification process, and the Zn-porphyrin-free base dipyrrin compounds 7a and 7b were obtained in ~70% yield (Scheme 8).

Route 3: Formation of a porphyrin from a dipyrrin-dipyrromethane. The reaction of a dipyrromethane and a dipyrromethane-dicarbinol provides a straightforward route to meso-substituted porphyrins (P. Rao, et al., *J. Org. Chem.*, 65, 7323-7344 (2000)). This approach is compatible with diverse substituents, particularly upon attachment to the dipyrromethane moiety. We sought to employ this method using a dipyrromethane bearing a dipyrrin. Several routes are available for the preparation of the precursor dipyrrin-benzaldehyde 2g. Oxidation of dipyrromethane-benzaldehyde 1g with p-chloranil in the presence of Zn(OAc)$_2$·2H$_2$O afforded Zn-2g in 81% yield (Scheme 3), but treatment with DTT gave the free-base dipyrrin 2g in only 31% yield (Scheme 4). For a more expedient synthesis, 1g was treated with p-chloranil in THF at room temperature for 24 h, giving the free-base dipyrrin in 60% yield (Scheme 9).

Scheme 9

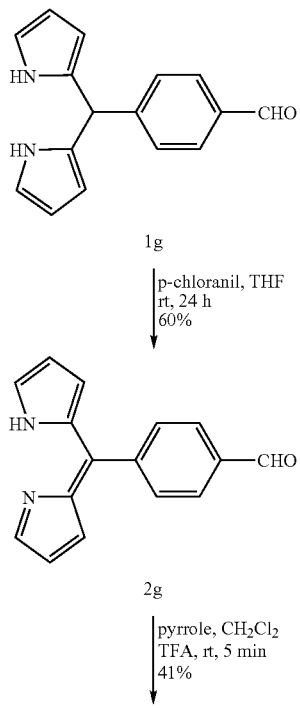

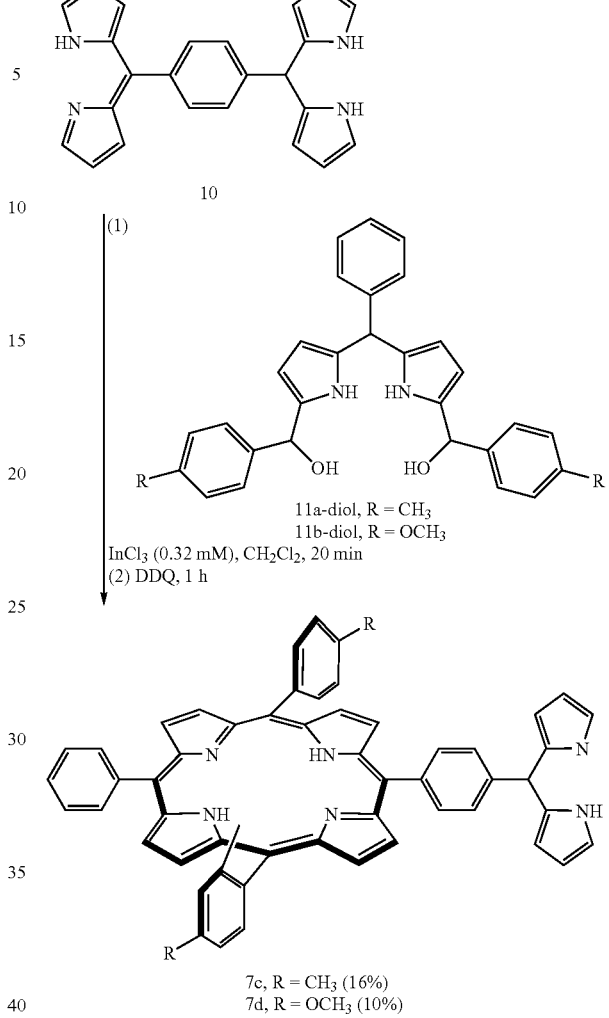

The condensation of 2g (1 equiv) with pyrrole (50 equiv) in CH$_2$Cl$_2$ in the presence of TFA (1.2 equiv) afforded compound 10. Analysis by $^1$H NMR spectroscopy indicated the presence of an impurity, which gave signals consistent with that for the N-confused dipyrromethane. The ratio of 10 and the N-confused isomer was 96:4, and the yield together was 41% (Scheme 9). The mixture could not be separated and was used directly in the subsequent condensations.

The condensation of 10 with dipyrromethane-dicarbinol 11a-diol in the presence of TFA (30 mM) in CH$_3$CN for up to 30 min followed by oxidation with DDQ failed to give the porphyrin. We next examined the condensation of 10 and 11a-diol under new catalysis conditions that employ mild Lewis acid catalysts in CH$_2$Cl$_2$ (G. Geier, III, et al., *J. Porphyrins Phthalocyanines*, 5, 810-823 (2001)). Thus, the condensation of 10 and 11a-diol in the presence of InCl$_3$ (0.32 mM) in CH$_2$Cl$_2$ followed by oxidation with DDQ gave the desired porphyrin 7c in 16% yield. Similarly, compound 7d was synthesized in 10% yield by condensation of 10 and 11b-diol in the presence of InCl$_3$ (0.32 mM) in CH$_2$Cl$_2$ followed by oxidation with DDQ. Two points concerning this approach are noteworthy. (1) Reaction of a dipyrrin (2a) and a dipyrromethane-dicarbinol (11a-diol) showed only a 2.5% yield of porphyrin, while a competition experiment of a dipyrrin (2b) and a dipyrromethane (1a) in the reaction with a dipyrromethane-dicarbinol (11a-diol) gave the porphyrin derived by exclusive reaction with the dipyrromethane. (2) Syntheses employing a mixed condensation of 2g, mesitaldehyde and pyrrole with $BF_3 \cdot OEt_2$/ethanol cocatalysis did not yield the porphyrin-dipyrrin, even with increased acid concentration and prolonged reaction time. The success of the dipyrromethane+dipyrromethane-dicarbinol condensation/oxidation in the presence of the dipyrrin highlights the mild conditions of this transformation.

F. Bis(porphyrin-dipyrrinato)metal triads. Triads composed of two zinc porphyrins and one zinc-dipyrrin complex were prepared as shown in Scheme 10. Treatment of 7a, 7b, 7c or 7d with $Zn(OAc)_2 \cdot 2H_2O$ afforded the desired $(ZnP-dp)_2Zn$ triads 12a, 12b, 12c or 12d in 83-97% yield. In each case the absorption spectral data indicated the reaction went to completion. Attempts to perform TLC analysis or column chromatography on silica, or SEC (analytical or preparative), however, resulted in disassembly of the bis(dipyrrinato)zinc unit and formation of the zinc porphyrin-free base dipyrrin. The laser desorption mass spectrometry (LD-MS) spectrum showed the expected molecule ion peak for the triad. Each triad was examined by fluorescence spectroscopy, which indicated the integrity of the zinc porphyrin.

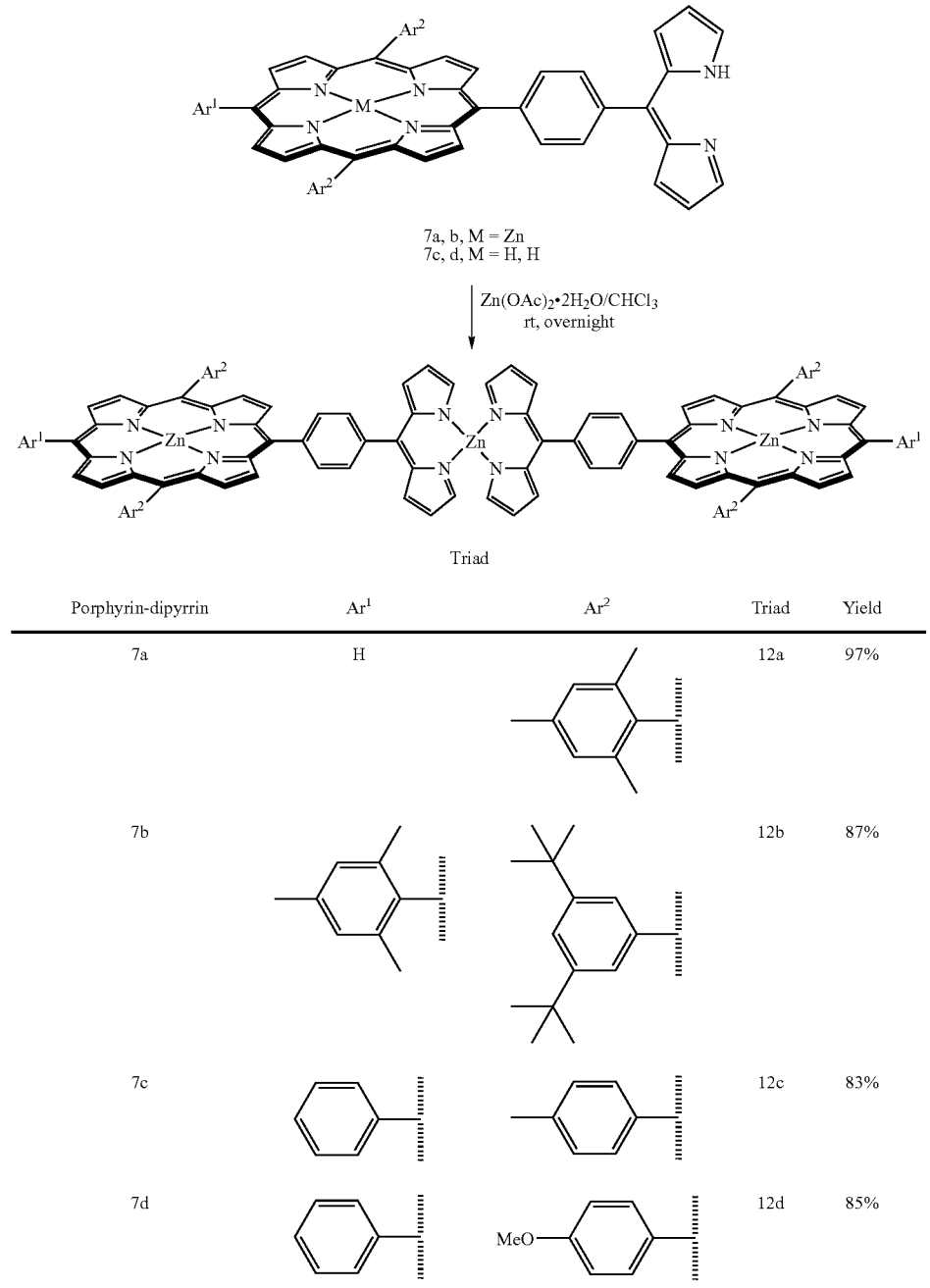

Scheme 10

G. A bis(dipyrrin)porphyrin triad. A porphyrin bearing two dipyrrins in a trans architecture was prepared for studies of self-assembly affording oligomers with alternating porphyrin and dipyrrins in the backbone. The synthesis of the bis(dipyrrin)-substituted porphyrin was achieved by two routes. The first route employs a dipyrrin-aldehyde in a porphyrin-forming reaction, while the second route entails the synthesis of a porphyrin-dipyrromethane, which is then oxidized to the porphyrin-dipyrrin.

Route 1: Condensation of a dipyrromethane and an aldehyde under TFA catalysis provides a trans-substituted porphyrin (B. Littler, et al., *J. Org. Chem.*, 64, 2864-2872 (1999)). Accordingly, condensation of 5-mesityldipyrromethane (1h) with dipyrrin-benzaldehyde 2g in the presence of catalytic amount of TFA followed by oxidation afforded the bis(dipyrrin)porphyrin 13 in 14% yield (Scheme 11).

Route 2: Condensation of 5-mesityldipyrromethane (1 h) with methyl 4-formylbenzoate under standard TFA-catalysis (B. Littler, et al., *J. Org. Chem.*, 64, 2864-2872 (1999)) provided the trans-substituted porphyrin 14 in 18% yield. Reduction of 14 with LiAlH$_4$ in THF afforded porphyrin-diol 15 in 89% yield, which upon oxidation with PCC in CH$_2$Cl$_2$ afforded bis(benzaldehyde)porphyrin 16 in 82% yield. Condensation of 16 with excess pyrrole under TFA catalysis (2.2 eq) in CH$_2$Cl$_2$ (50 mM) gave the bis(dipyrromethane)porphyrin 17 in 72% yield. Oxidation of 7 with DDQ in THF provided the desired bis(dipyrrin)porphyrin 13 in 23% yield (Scheme 12).

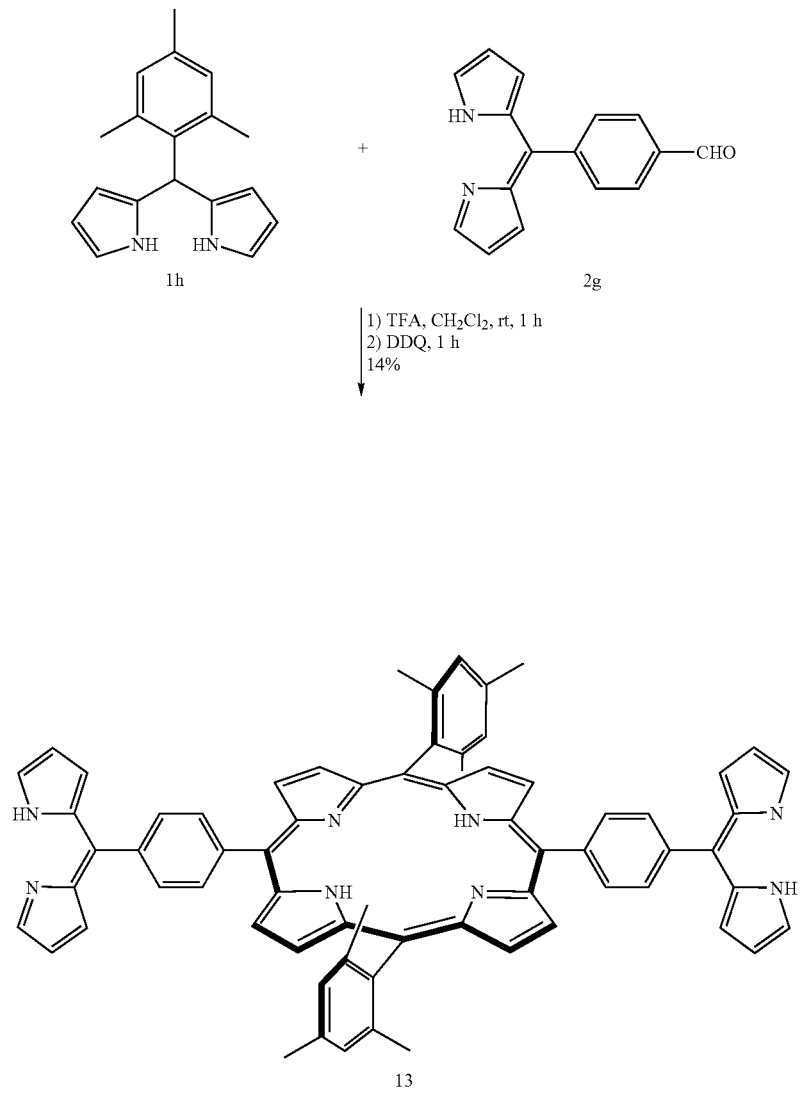

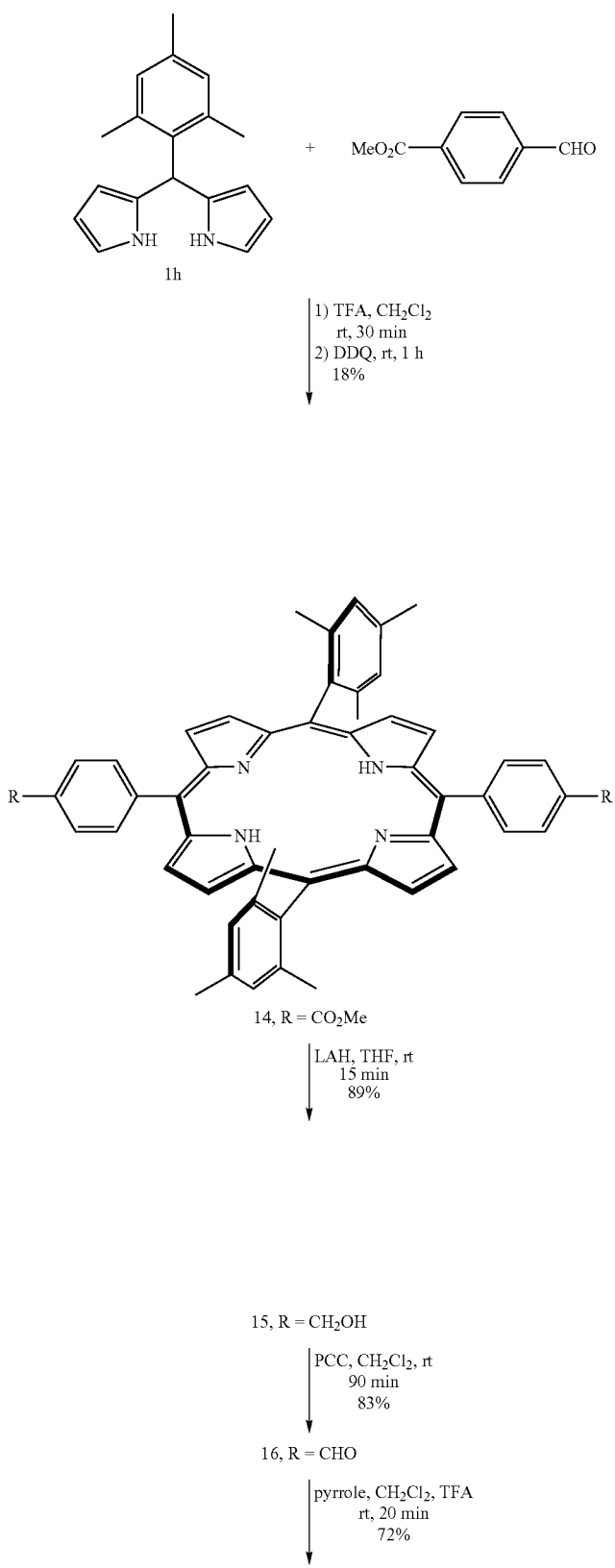
Scheme 12

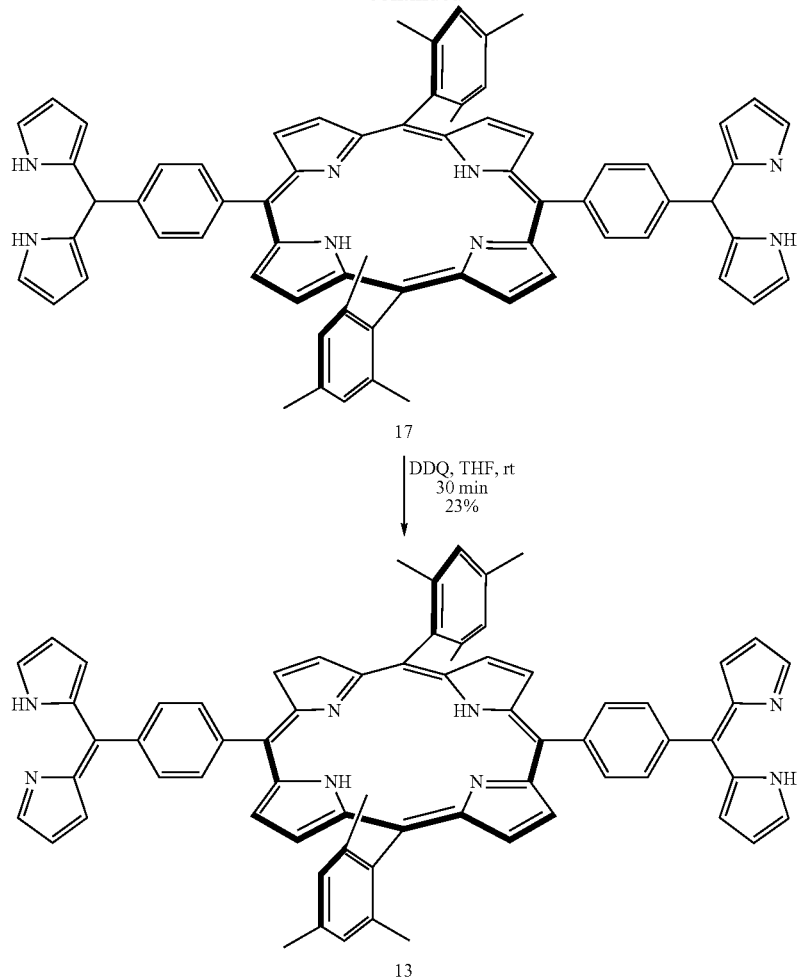

II. Characterization

A. Chemical characterization. The free base dipyrrins and metal derivatives were generally assessed for purity by TLC and characterized by absorption spectroscopy, $^1$H NMR spectroscopy, $^{13}$C NMR spectroscopy (except Pd-2c), and FAB-MS. Acceptable elemental analyses were obtained except for 2a-c, 2g, Pd-2b, Zn-2g, and 10. The porphyrins and triads were characterized by absorption and fluorescence spectroscopy, $^1$H NMR spectroscopy, and LD-MS. Note that the bis (dipyrrinato)zinc(II) complexes remained intact upon exposure to silica gel (TLC or column chromatography) while the all-zinc containing triads (ZnP-dp)$_2$Zn disassembled upon exposure to silica.

The $^1$H NMR spectra of all free base dipyrrins and their metal complexes display simple coupling patterns derived from the protons on the dipyrrin units. However, the $^1$H NMR spectrum (in CDCl$_3$) of the free base dipyrrins showed no peak for the NH proton in the dipyrrin moiety. Similarly, $^{13}$C NMR spectra of free base dipyrrins and their metal complexes showed simple peaks owing to the carbons in the two pyrrolic rings.

B. Absorption and emission spectroscopy. The absorption and emission spectra of the (ZnP-dp)$_2$Zn triads 12a and 12b are shown in FIGS. 1a and 1b. In each case, the absorption spectrum is essentially the sum of the spectra of the component parts. The bands due to the bis(dipyrrinato)zinc unit are clearly displayed between the porphyrin Soret (B) and Q bands. However, illumination of the triad at 485 nm, where the bis(dipyrrinato)zinc unit absorbs predominantly, results in emission almost exclusively from the zinc porphyrin. These data are consistent with energy transfer from the excited-state of the bis(dipyrrinato)zinc unit to the adjacent zinc porphyrin.

III. Discussion

Dyes must meet a number of challenging criteria for use as accessory pigments with porphyrins. The bis(dipyrrinato) zinc complexes are non-polar (i.e., neutral) thereby facilitating chemical manipulations, form by self-assembly from the free base dipyrrin, and provide spectral coverage in the green, a region where porphyrins absorb poorly. Oxidation of dipyrromethanes with DDQ or p-chloranil in the presence of Zn(OAc)$_2$.2H$_2$O proved to be an efficient method to prepare the corresponding bis(dipyrrinato)zinc(II) complexes. The bis(dipyrrinato)zinc complexes are robust, remaining assembled in solution, but can be disassembled selectively. Three different routes to prepare porphyrin-dipyrrins were developed. We found that only the bis(dipyrrinato)palladium (II) complex can be employed as the Suzuki coupling partner. The self-assembling property of bis(dipyrrinato)metal complexes provides unique opportunities, in that the complexes constitute both a linker and an accessory pigment. Static emission spectroscopy and time-resolved absorption spectroscopy of two (ZnP-dp)$_2$Zn triads (12a, 12b) indicated efficient energy transfer from the bis(dipyrrinato)zinc complex to the zinc porphyrin.

The approach for preparing the self-assembled triads described herein was inspired by the work of Collin, Sauvage, and Flamigni aimed at preparing analogous triads based on terpyridyl-metallo complexes bridging two porphyrins in a linear array) L. Flamigni, et al., *Coord. Chem. Rev.*, 190-192, 671-682 (1999); A. Harriman and J.-P. Sauvage, *Chem. Soc. Rev.*, 25, 41-48 (1996); L. Flamigni, et al., *Chem. Eur. J.*, 4, 1744-1754 (1998); I. Dixon, et al., *Inorg. Chem.*, 40, 5507-5517 (2001); L. Flamigni, et al., *J. Phys. Chem. B*, 106, 6663-6671 (2002)). The synthesis of the latter arrays can be done in a directed manner, affording unsymmetrical triads (M$^1$P-terpy)M(terpy-M$^2$P) (L. Flamigni, et al., *Chem. Eur. J.*, 4, 1744-1754 (1998); I. Dixon, et al., *Inorg. Chem.*, 40, 5507-5517 (2001)). No such directed methods yet exist for the rational synthesis of unsymmetrical dipyrrin-metal complexes. On the other hand, the terpy-based triads generally have been designed to undergo photoinduced electron transfer among the three components, though some energy-transfer processes have been elicited with iridium-terpy complexes, and this was with UV illumination (L. Flamigni, et al., *J. Phys. Chem. B*, 106, 6663-6671 (2002)). The bis(dipyrrinato)zinc complexes undergo efficient energy transfer following excitation and thus constitute viable accessory pigments for the attached porphyrins.

Experimental Section

General. $^1$H NMR spectra (300 or 400 MHz) and $^{13}$C NMR spectra (75 or 100 MHz) were collected in CDCl$_3$. Absorption spectra and fluorescence spectra were collected in CH$_2$Cl$_2$ or toluene at room temperature. Mass spectra of porphyrins were obtained via laser desorption mass spectrometry (LD-MS) in the absence of an added matrix (N. Srinivasan, et al., *J. Porphyrins Phthalocyanines*, 3, 283-291 (1999); D. Fenyo, et al., *J. Porphyrins Phthalocyanines*, 1, 93-99 (1997)), or by high resolution fast atom bombardment mass spectrometry (FAB-MS). All reagents were obtained from Aldrich and were used as received. The known compounds 1a-c (B. Littler, et al., *J. Org. Chem.*, 64, 1391-1396 (1999)), 1d (L. Yu and J. Lindsey, *Tetrahedron*, 57, 9285-9298 (2001)), 1e (B. Littler, et al., *J. Org. Chem.*, 64, 1391-1396 (1999); Q. Wang and D. Bruce, *SYNLETT*, 1267-1268 (1995)), 1f (P. Rao, et al., *J. Org. Chem.*, 65, 7323-7344 (2000)), 1g (P. Rao, et al., *J. Org. Chem.*, 65, 7323-7344 (2000)), 1h, 1i (D. Hammel, et al., *Adv. Mater.*, 4, 737-739 (1992)), 8b (L. Yu and J. Lindsey, *Tetrahedron*, 57, 9285-9298 (2001)), 11a (P. Rao, et al., *J. Org. Chem.*, 65, 7323-7344 (2000)), 11b (P. Rao, et al., *J. Org. Chem.*, 65, 7323-7344 (2000)), 11a-diol (P. Rao, et al., *J. Org. Chem.*, 65, 7323-7344 (2000)) and 11b-diol (P. Rao, et al., *J. Org. Chem.*, 65, 7323-7344 (2000)) were prepared according to literature procedures.

Solvents. All solvents were dried by standard methods. Toluene was distilled from CaH$_2$. Anhydrous DMF, 1,2-dimethoxyethane, CH$_2$Cl$_2$ and CHCl$_3$ (certified ACS grade stabilized with 0.8% ethanol) were used as received.

Chromatography. Adsorption column chromatography was performed using flash silica gel (Baker, 60-200 mesh). Preparative-scale size exclusion chromatography (SEC) was performed using BioRad Bio-beads SX-1 in THF (HPLC grade). Analytical SEC (R. Wagner, et al., *J. Am. Chem. Soc.*, 118, 11166-11180 (1996)) ($\lambda$=420 nm) was performed to monitor the progress of the coupling reactions.

Synthesis of Dipyrrins by Oxidation of a Dipyrromethane:

5-Phenyldipyrrin (2a). To a solution of 1a (666 mg, 3.00 mmol) in THF (10 mL) was added dropwise a solution of DDQ (681 mg, 3.00 mmol, one molar equivalent) in THF (10 mL). TLC analysis (silica, CHCl$_3$) indicated complete consumption of the starting materials after stirring for 1 h at room temperature. The mixture was poured into H$_2$O, extracted with CHCl$_3$ and dried (Na$_2$SO$_4$). Column chromatography [silica, CHCl$_3$/MeOH, (99:1)] afforded a brown oil which partially solidified upon storage overnight at 0° C. (280 mg, 42%): mp 176-178° C.; $^1$H NMR δ 6.39 (dd, J$^1$=1.2 Hz, J$^2$=4.2 Hz, 2H), 6.60 (d, J=4.2 Hz, 2H), 7.43-7.52 (m, 5H), 7.65 (s, 2H); $^{13}$C NMR δ 117.5, 127.5, 128.9, 129.1, 130.7, 137.2, 140.5, 143.6; FAB-MS obsd 221.1068 (M$^+$+H), calcd 221.1079 (C$_{15}$H$_{12}$N$_2$); $\lambda_{abs}$ (CH$_2$Cl$_2$, log ∈) 309 (3.84), 432 (4.28) nm.

5-(4-tert-Butylphenyl)dipyrrin (2b). Following the procedure described for the preparation of 2a, a sample of 1b (834 mg, 3.00 mmol) in THF (10 mL) was treated with a solution of DDQ (681 mg, 3.00 mmol) in THF (10 mL) for 1 h at room temperature. Removal of solvent and chromatography [silica, CHCl$_3$/MeOH (98:2)] afforded a brown-black solid (415 mg, 51%): mp 148-150° C.; $^1$H NMR δ 1.39 (s, 9H), 6.39 (dd, J$^1$=1.6 Hz, J$^2$=5.6 Hz, 2H), 6.66 (d, J=5.6 Hz, 2H), 7.44 (s, 4H), 7.64 (s, 2H); $^{13}$C NMR δ 31.3, 34.7, 117.4, 124.5, 128.9, 130.7, 134.3, 140.9, 142.3, 143.3, 152.1; LD-MS obsd 274.8; FAB-MS obsd 277.1707 (M$^+$+H), calcd 277.1705 (C$_{19}$H$_{20}$N$_2$). Anal. Calcd: C, 82.57; H, 7.29; N, 10.14. Found: C, 82.15; H, 7.37; N, 9.93; $\lambda_{abs}$ (CH$_2$Cl$_2$), log ∈) 327 (3.97), 433 (4.36) nm.

5-(4-Formylphenyl)dipyrrin (2g). A solution of 1g (1.15 g, 4.60 mmol) in THF (46 mL) was treated with p-chloranil (1.13 g, 4.60 mmol). The reaction mixture was stirred at room temperature for 24 h. The mixture was diluted with CHCl$_3$, washed with water and dried (Na$_2$SO$_4$). The solvent was evaporated under reduced pressure to afford a dark residue. The dark residue obtained was chromatographed [silica, hexanes/ethyl acetate (3:1)], affording an orange solid (0.68 g, 60%). The analytical data were identical with those obtained for the product prepared by demetalation of Zn-2g.

5-(Mesityl)dipyrrin (2h). Following the procedure described for the preparation of 2a, a solution of 1h (264 mg, 1.00 mmol) in THF (5 mL) was treated with a solution of DDQ (227 mg, 1.00 mmol) in THF (3 mL) for 30 min at room temperature. Removal of solvent and chromatography [silica, CH$_2$Cl$_2$/MeOH (98:2)] afforded a brown solid (150 mg, 57%): mp 114-116° C.; $^1$H NMR δ 2.08 (s, 6H), 2.35 (s, 3H), 6.32 (d, J=4.4 Hz, 2H), 6.40 (d, J=4.4 Hz, 2H), 6.91 (s, 2H), 7.62 (s, 2H); $^{13}$C NMR δ 19.9, 21.1, 117.6, 117.7, 127.3, 127.7, 133.4, 136.6, 137.4, 140.5, 140.9; LD-MS obsd 261.7, calcd avg mass 262.4 (C$_{18}$H$_{18}$N$_2$); Anal. Calcd: C, 82.41; H, 6.92; N, 10.68. Found: C, 81.63; H, 6.97; N, 10.37; $\lambda_{abs}$ (CH$_2$Cl$_2$) 431 nm 5-(Pentafluorophenyl)dipyrrin (2j). Following the procedure described for the preparation of 2a, a sample of 1j (624 mg, 2.00 mmol) in THF (5 mL) was treated with a solution of DDQ (454 mg, 2.00 mmol) in THF (5 mL) at room temperature. TLC analysis [silica, hexanes/CH$_2$Cl$_2$ (1:1)] after 40 min showed incomplete oxidation, therefore additional amount of DDQ (91 mg, 0.40 mmol) in THF (2 mL) was added and stirred for another 20 min at room temperature. Removal of solvent and chromatography [silica, hexanes/CH$_2$Cl$_2$ (1:1)] afforded a brown-yellowish solid (530 mg, 85%): mp 116-117° C.; $^1$H NMR δ 6.42 (dd, J$^1$=1.2 Hz, J$^2$=4.0 Hz, 2H), 6.47 (d, J=4.0 Hz, 2H), 7.66 (s, 2H); $^{13}$C NMR δ 118.9, 123.8, 126.8, 140.3, 145.4. Anal. Calcd: C, 58.07; H, 2.27; N, 9.03. Found: C, 58.21; H, 2.19; N, 9.06 ($C_{15}H_7F_5N_2$); $\lambda_{abs}$ ($CH_2Cl_2$) 430 nm.

Synthesis of Bis(Dipyrrinato)Metal Complexes by Metalation of Dipyrrins:

Bis[5-(4-tert-butylphenyl)dipyrrinato]copper(II) (Cu-2b). A solution of 2b (113 mg, 0.410 mmol) in $CH_2Cl_2$ (10 mL) was treated with a suspension of $Cu(OAc)_2 \cdot H_2O$ (204 mg, 1.02 mmol, 2.5 molar equivalents) in methanol (~3 mL). The mixture was stirred at room temperature for 10 min. UV-vis spectroscopic analysis showed no remaining free base dipyrrin. The reaction mixture was then diluted with $CH_2Cl_2$ (30 mL) and washed with $H_2O$. The organic layer was separated and dried ($Na_2SO_4$). Chromatography (silica, $CH_2Cl_2$) afforded a brown solid (104 mg, 82%): mp>280° C.; LD-MS obsd 611.5, FAB-MS obsd 613.2408, calcd 613.2392 ($C_{38}H_{38}CuN_4$); Anal. Calcd: C, 74.30; H, 6.24; N, 9.12. Found: C, 74.19; H, 6.37; N, 8.91; 2, $\lambda_2$ ($CH_2Cl_2$, log ∈) 342 (4.38), 466 (4.83), 499 (4.54) nm.

Bis[(4-tert-butylphenyl)dipyrrinato]palladium(II) (Pd-2b). A solution of 2b (28 mg, 0.10 mmol) in $CHCl_3$ (2.0 mL) and TEA (0.50 mL) was treated with $Pd_2(dba)_3$ (228 mg, 0.250 mmol) in methanol (1 mL) overnight at room temperature. The mixture was diluted with $CHCl_3$ (5 mL) and filtered through a pad of silica gel ($CHCl_3$). Chromatography (silica, $CHCl_3$) afforded a red-orange solid (28 mg, 85%): mp>280° C.; $^1H$ NMR δ 1.42 (s, 18H), 6.36 (dd, $J^1$=1.6 Hz, $J^2$=4.4 Hz, 4H), 6.77 (dd, $J^1$=1.6 Hz, $J^2$=4.4 Hz, 4H), 7.41 (s, 4H), 7.48 (d, J=8.0 Hz, 4H), 7.52 (d, J=8.0 Hz, 4H); $^{13}C$ NMR δ 31.4, 34.8, 116.6, 124.3, 130.3, 131.3, 134.6, 137.2, 148.2, 151.5, 151.8; FAB-MS obsd 656.2166, calcd 656.2131 ($C_{38}H_{38}N_4Pd$); Anal. Calcd: C, 69.45; H, 5.83; N, 8.53. Found: C, 68.74; H, 6.00; N, 7.88; $\lambda_{abs}$ ($CH_2Cl_2$, log ∈) 342 (4.42), 376 (4.32), 479 (5.02) nm.

Bis[5-(4-iodophenyl)dipyrrinato] palladium(II) (Pd-2c). A solution of 2c (140 mg, 0.40 mmol) in $CH_2Cl_2$ (5 mL) was treated with $Pd(OAc)_2$ (90 mg, 0.40 mmol) at room temperature. UV-vis and TLC analysis (silica, $CHCl_3$) indicated complete metalation after 20 min. Removal of solvent and chromatography (silica, $CH_2Cl_2$) afforded a yellow-orange solid (80 mg, 50%): mp>280° C.; $^1H$ NMR δ 6.37 (dd, $J^1$=1.2 Hz, $J^2$=4.0 Hz, 4H), 6.69 (d, J=4.0 Hz, 4H), 7.32 (d, J=8.4 Hz, 4H), 7.39 (m, 4H), 7.83 (d, J=8.4 Hz, 4H); LD-MS obsd 752.8 calcd 753.9 ($C_{30}H_{20}I_2N_4Pd$); Anal Calcd: C, 45.22; H, 2.53; N, 7.03. Found: C, 45.26; H, 2.51; N, 6.78; 2, $\lambda_{abs}$ ($CHCl_3$, log ∈) 333 (br, 4.19), 385 (br, 4.11), 482 (4.78) nm.

Two-Step Synthesis of a Bis(Dipyrrinato)Metal Complex from the Dipyrromethane:

Bis[5-(4-iodophenyl)dipyrrinato]palladium(II) (Pd-2c). A solution of 1c (5.27 g, 15.1 mmol) in THF (150 mL) was treated overnight with p-chloranil (3.71 g, 15.1 mmol) at room temperature. Solvent was removed and the residue was collected in $CH_2Cl_2$ (150 mL), sonicated and filtered to remove the quinone species. The filtrate was concentrated, affording a brown solid. This crude product was dissolved in $CH_2Cl_2$ (150 mL) and was treated with $Pd(OAc)_2$ (6.78 g, 30.2 mmol) at room temperature. TLC and UV-vis analysis indicated complete metalation after 20 min. The red-orange solid precipitated from the reaction mixture. Filtration and washing with $CH_2Cl_2$ afforded a red-orange solid (2.46 g, 43%). The analytical data were identical with those obtained for the product prepared by metalation of the dipyrrin. The one-flask oxidation/complexation process employed to form zinc-dipyrrin complexes applied to 1c using p-chloranil and $Pd(OAc)_2$ in THF gave slow reaction and afforded the product Pd-2c in only 30% yield.

One-Flask Syntheses of Bis(Dipyrrinato)Zinc Complexes from the Dipyrromethane:

Bis(5-phenyldipyrrinato)zinc(II) (Zn-2a). A mixture of 1a (111 mg, 0.500 mmol) and $Zn(OAc)_2 \cdot 2H_2O$ (274 mg, 1.25 mmol) in THF (5 mL) was treated all-at-once with p-chloranil (123 mg, 0.500 mmol). TLC (silica, $CHCl_3$) showed no dipyrromethane remained after stirring for 27 h at room temperature. Solvent was removed and the residue was dissolved in $CHCl_3$. The organic phase was washed with aqueous $NaHCO_3$, $H_2O$ and dried ($Na_2SO_4$). Chromatography [silica, $CHCl_3 \rightarrow CHCl_3$/MeOH (98:2)] afforded a yellow solid. $^1H$ NMR analysis of this product showed a mixture of the free base dipyrrin and the zinc(II)-dipyrrin complex. This mixture was dissolved in $CHCl_3$ (5 mL) and treated with $Zn(OAc)_2 \cdot 2H_2O$ (274 mg, 1.25 mmol) in methanol (1 mL) at room temperature. After stirring overnight, standard work up and chromatography (silica, $CHCl_3$) afforded a yellow solid (102 mg, 81%): mp 225-227° C.; $^1H$ NMR δ 6.40 (dd, $J^1$=4.0 Hz, $J^2$=1.2 Hz, 6H), 6.71 (d, J=3.6 Hz, 6H), 7.44-7.50 (m, 4H), 7.55-7.58 (m, 6H); $^{13}C$ NMR δ 117.0, 127.1, 128.4, 130.6, 132.9, 139.0, 140.6, 148.7, 149.7; FAB-MS obsd 502.1172, calcd 502.1136 ($C_{30}H_{22}N_4Zn$); Anal. Calcd: C, 71.50; H, 4.40; N, 11.12. Found: C, 71.29; H, 4.56; N, 11.21; $\lambda_{abs}$ ($CH_2Cl_2$, log ∈) 322 (br, 4.14), 482 (5.06) nm. Alternatively, the same mixture of 1a and $Zn(OAc)_2 \cdot 2H_2O$ in THF (5 mL) was treated dropwise with a solution of DDQ (114 mg, 0.500 mmol) in THF (1 mL) for 40 min at room temperature. The same workup procedure afforded a yellow solid (99 mg, 78%) with identical analytical data.

Bis[5-(4-tert-butylphenyl)dipyrrinato]zinc(II) (Zn-2b). A mixture of 1b (115 mg, 0.413 mmol) and $Zn(OAc)_2 \cdot 2H_2O$ (227 mg, 1.03 mmol, 2.5 eq) in THF (5 mL) was treated with p-chloranil (102 mg, 0.413 mmol) overnight at room temperature. The reaction mixture was poured into $H_2O$, and extracted with $CHCl_3$ and dried ($Na_2SO_4$). The solvent was removed and the residue was collected into $CHCl_3$ (5 mL) and was treated with $Zn(OAc)_2 \cdot 2H_2O$ (227 mg, 0.413 mmol) in methanol (1.0 mL) overnight at room temperature. Standard workup and chromatography (silica, $CH_2Cl_2$), afforded a yellow solid (105 mg, 82%): mp>280° C.; $^1H$ NMR δ 1.41 (s, 18H), 6.39-6.41 (m, 4H), 6.76 (d, J=4.2 Hz, 4H), 7.46 (d, J=8.4 Hz, 4H), 7.50 (d, J=8.4 Hz, 4H), 7.53 (s, br, 4H); $^{13}C$ NMR δ 31.4, 34.7, 116.8, 124.0, 130.6, 133.0, 136.1, 140.7, 149.2, 149.5, 151.6; FAB-MS obsd 614.2392, calcd 614.2388 ($C_{38}H_{38}N_4Zn$). Anal. Calcd: C, 74.08; H, 6.22; N, 9.09. Found: C, 73.43; H, 6.18; N, 8.96; $\lambda_{abs}$ ($CH_2Cl_2$, log ∈) 338 (br, 4.30), 482 (5.06) nm.

Bis[5-(4-iodophenyl)dipyrrinato]zinc(II) (Zn-2c). A mixture of 1c (1.92 g, 5.51 mmol) and $Zn(OAc_2 \cdot 2H_2O$ (3.02 g, 13.8 mmol, 2.5 eq) in THF (75 mL) was treated with p-chloranil (1.35 g, 5.51 mmol). After stirring overnight at room temperature, the entire reaction mixture was filtered through a short pad of silica gel, which was then washed with THF. Solvent was removed and the residue was collected in $CHCl_3$ (100 mL). $Zn(OAc)_2 \cdot 2H_2O$ (1.21 g, 5.51 mmol) in methanol (10 mL) was added and the mixture was stirred overnight at room temperature. The reaction mixture was then washed with aqueous $NaHCO_3$, $H_2O$ and dried ($Na_2SO_4$). The organic layer was dried ($Na_2SO_4$), concentrated, and chromatographed (silica, $CHCl_3$), affording a yellow solid. The solid was washed (sonicated) with methanol (1.35 g, 65%): mp>280° C.; $^1H$ NMR δ 6.42 (dd, $J^1$=1.2 Hz, $J^2$=4.4 Hz, 4H), 6.69-6.70 (m, 4H), 7.30 (d, J=8.0 Hz, 4H), 7.53 (s, br, 4H), 7.81 (d, J=8.0 Hz, 4H); $^{13}C$ NMR δ 117.4, 132.3, 132.7, 136.4, 138.4, 140.2, 147.2, 150.1; LD-MS obsd 756.9 calcd 753.9 ($C_{30}H_{20}I_2N_4Zn$); Anal Calcd: C, 47.68; H, 2.67; N, 7.41. Found: C, 47.83; H, 2.71; N, 7.38; $\lambda_{abs}$ ($CH_2Cl_2$, log ∈) 333 (br, 4.29), 485 (5.08) nm Bis[5-[4-(4,4,5,5-tetramethyl -1,3,2-dioxaborolan-2-yl) phenyl]dipyrrinato]zinc(II) (Zn-2d). A mixture of 1d (348 mg, 1.00 mmol) and $Zn(OAc)_2.2H_2O$ (549 mg, 2.50 mmol) in THF (14 mL) was treated overnight with p-chloranil (246 mg, 1.00 mmol) at room temperature. The mixture was poured into $H_2O$ and extracted with $CHCl_3$. The organic layer was dried ($Na_2SO_4$) and chromatographed [silica, $CHCl_3 \rightarrow CHCl_3$/methanol (95:5)], affording a yellow solid. The solid was dissolved in $CHCl_3$ and precipitated with methanol (321 mg, 85%): mp 272° C. (dec); $^1H$ NMR δ 1.40 (s, 24H), 6.40 (dd, $J^1$=1.2 Hz, $J^2$=4.2 Hz, 4H), 6.69 (dd, $J^1$=1.2 Hz, $J^2$=4.2 Hz, 4H), 7.53 (br, s, 4H), 7.58 (d, J=8.4 Hz, 4H), 7.90 (d, J=8.4 Hz, 4H); $^{13}C$ NMR (100 MHz) δ 24.93, 84.01, 117.08, 129.98, 132.86, 133.42, 140.35, 141.80, 148.59, 149.78; LD-MS obsd 752.5, calcd exact mass 754.3 ($C_{42}H_{44}B_2N_4O_4Zn$); Anal. Calcd: C, 66.74; H, 5.87; N, 7.41. Found: C, 66.87; H, 5.78; N, 7.45; $\lambda_{abs}$ ($CH_2Cl_2$, log ∈) 323 (br, 4.26), 483 (5.07) nm.

Bis[5-(4-formylphenyl)dipyrrinato]zinc(II) (Zn-2g). A solution of 1g (1.15 g, 4.60 mmol) in THF (46 mL) was treated with $Zn(OAc)_2.2H_2O$ (2.52 g, 11.5 mmol) and p-chloranil (1.13 g, 4.60 mmol). The reaction mixture was stirred at room temperature for 20 h. The mixture was diluted with $CHCl_3$, washed with water and dried ($Na_2SO_4$). The solvent was evaporated under reduced pressure to afford a dark residue. The dark residue obtained was chromatographed [silica, $CH_2Cl_2$/ethyl acetate (9:1)], affording an orange solid. The orange solid was washed with methanol (to remove any quinone species present) to afford an orange solid (1.05 g, 81%): mp 221-223° C.; $^1H$ NMR δ 6.44 (dd, $J^1$=1.2 Hz, $J^2$=4.4 Hz, 4H), 6.64 (dd, $J^1$=0.8 Hz, $J^2$=4.4 Hz, 4H), 7.58 (s, 4H), 7.75 (d, J=8.0 Hz, 4H), 8.01 (d, J=8.0 Hz, 4H), 10.16 (s, 2H); $^{13}C$ NMR δ 117.75, 128.69, 131.40, 132.75, 136.35, 140.00, 145.16, 146.77, 191.91. Anal. Calcd for $C_{32}H_{22}N_4O_2Zn$: C, 68.08; H, 3.87; N, 10.24. Found: C, 68.88; H, 3.95; N, 9.99; $\lambda_{abs}$ ($CH_2Cl_2$) 486 nm.

Bis[5-(mesityl)dipyrrinato]zinc(II) (Zn-2h). A mixture of 1h (264 mg, 1.00 mmol) and $Zn(OAc)_2.2H_2O$ (549 mg, 2.50 mmol) in THF (10 mL) was treated with p-chloranil (248 mg, 1.00 mmol) overnight at room temperature. Removal of solvent and chromatography (silica, $CH_2Cl_2$) afforded an orange solid. The orange solid was washed with methanol and dried giving an orange solid (253 mg, 86%): mp 254-256° C.; $^1H$ NMR δ 2.18 (s, 12H), 2.38 (s, 6H), 6.35 (d, J=4.0 Hz, 4H), 6.58 (d, J=4.0 Hz, 4H), 6.95 (s, 4H), 7.47 (s, 4H); C NMR (J. Lindsey, et al., *Tetrahedron*, 50, 8941-8968 (1994)) (100 MHz) δ 19.9, 21.1, 117.1, 127.6, 131.1, 135.4, 136.4, 137.1, 140.0, 148.2, 149.1; MALDI-MS (dithranol) obsd 586.5, calcd avg mass 588.1 ($C_{36}H_{34}N_4Zn$); Anal. Calcd: C, 73.53; H, 5.83; N, 9.53. Found: C, 73.21; H, 5.78; N, 9.47; $\lambda_{abs}$ ($CH_2Cl_2$) 345 (br), 485 nm.

Bis[5-(pentafluorophenyl)dipyrrinato]zinc(II) (Zn-2j). A mixture of 1j (312 mg, 1.00 mmol) and $Zn(OAc)_2.2H_2O$ (549 mg, 2.50 mmol) in THF (10 mL) was treated with DDQ (272 mg, 1.20 mmol) for 40 min at room temperature. The reaction mixture was filtered through a pad of silica, washed with $CH_2Cl_2$. The solvent was removed and the residue was dissolved in $CH_2Cl_2$ (30 mL) and was treated with a solution of $Zn(OAc)_2.2H_2O$ (549 mg, 2.50 mmol) in methanol (5.0 mL) overnight at room temperature. The reaction mixture was washed with aqueous $NaHCO_3$, $H_2O$ and dried ($Na_2SO_4$). Chromatography [silica, hexanes/$CH_2Cl_2$ (1:1)] afforded an orange-red solid, which was washed with methanol (190 mg, 55%): mp 266-268° C.; $^1H$ NMR δ 6.46 (d, J=4.0 Hz, 4H), 6.67 (d, J=4.0 Hz, 4H), 7.59 (s, 4H); $^{13}C$ NMR δ 118.7, 130.4, 131.2, 139.5, 151.7. Anal. Calcd: C, 52.69; H, 1.77; N, 8.19. Found: C, 52.66; H, 1.73; N, 8.14 ($C_{30}H_{12}F_{10}N_4Zn$); $\lambda_{abs}$ ($CH_2Cl_2$) 496 nm. Alternatively, the same mixture of 1j (312 mg, 1.00 mmol) and $Zn(OAc)_2.2H_2O$ (547 mg, 2.50 mmol) in THF (10 mL) was treated overnight with p-chloranil (297 mg, 1.20 mmol) at room temperature. The same workup procedure afforded an orange-red solid (105 mg, 31%) with identical analytical data.

Synthesis of Dipyrrins Via DTT-Mediated Demetalation of Bis(Dipyrrinato)Metal Complexes:

5-Phenyldipyrrin (2a). A solution of Zn-2a (163 mg, 0.323 mmol) in $CH_2Cl_2$ (60 mL) was treated with DTT (498 mg, 3.23 mmol, 10 molar equivalents) at room temperature. TLC and UV-vis analysis showed complete demetalation after 30 min. The reaction mixture was diluted with $CH_2Cl_2$, washed with $H_2O$ and dried ($Na_2SO_4$). Removal of solvent and chromatography [silica, ethyl acetate/hexanes (1:2)] afforded a slightly brown solid (114 mg, 80%). The analytical data were identical with those obtained for the product prepared by direct oxidation of the dipyrromethane.

5-(4-tert-Butylphenyl)dipyrrin (2b) from demetalation of Cu-2b. A solution of Cu-2b (50 mg, 0.081 mmol) in $CH_2Cl_2$ (15 mL) was treated with DTT (125 mg, 0.81 mmol, 10 molar equivalents) at room temperature. TLC and UV-vis analysis showed complete demetalation after 10 min. The reaction mixture was diluted with $CH_2Cl_2$, washed with $H_2O$ and dried ($Na_2SO_4$). Removal of solvent and chromatography [silica, ethyl acetate/hexanes (1:2)] afforded a slightly brown solid (43 mg, 95%). The analytical data were identical with those obtained for the product prepared by direct oxidation of the dipyrromethane.

5-(4-tert-Butylphenyl)dipyrrin (2b) from demetalation of Pd-2b. A solution of Pd-2b (34 mg, 0.052 mmol) in $CH_2Cl_2$ (10 mL) was treated with DTT (80 mg, 0.52 mmol, 10 molar equivalents) at room temperature. TLC and UV-vis analysis showed complete demetalation after 17 h. The reaction mixture was diluted with $CH_2Cl_2$, washed with $H_2O$ and dried ($Na_2SO_4$). Removal of solvent and chromatography [silica, ethyl acetate/hexanes (1:2)] afforded a slightly brown solid (23 mg, 79%). The analytical data were identical with those obtained for the product prepared by direct oxidation of the dipyrromethane.

5-(4-Iodophenyl)dipyrrin (2c) from demetalation of Zn-2c. A solution of Zn-2c (227 mg, 0.300 mmol) in $CH_2Cl_2$ (30 mL) was treated with DTT (462 mg, 3.00 mmol, 10 eq) at room temperature. UV-vis analysis indicated complete demetalation after 30 min. Then the reaction mixture was washed with $H_2O$ three times and dried ($Na_2SO_4$). Removal of solvent and chromatography (silica, $CH_2Cl_2$) afforded a brown solid (176 mg, 85%): mp 145° C. (dec); $^1H$ NMR δ 6.41 (dd, $J^1$=1.6 Hz, $J^2$=4.4 Hz, 2H), 6.58-6.59 (m, 2H), 7.23 (d, J=8.4 Hz, 2H), 7.67 (s 2H), 7.79 (d, J=8.4 Hz, 2H); $^{13}C$ NMR δ 117.7, 130.5, 132.5, 136.9, 144.0; LD-MS obsd 345.6; FAB-MS obsd 347.0045 ($M^+$+H), calcd 347.0053 ($C_{15}H_{11}IN_2$); $\lambda_{abs}$ ($CH_2Cl_2$, log ∈) 320 (3.98), 433 (4.33) nm.

5-(4-Iodophenyl)dipyrrin (2c) from demetalation of Pd-2c. A suspension of Pd-2c (159 mg, 0.200 mmol) in $CH_2Cl_2$ (40 mL) was treated with DTT (308 mg, 2.00 mmol, 10 eq) at room temperature. UV-vis analysis indicated complete demetalation after 18 h. Then the reaction mixture was washed with $H_2O$ three times and dried ($Na_2SO_4$). Removal of solvent and chromatography [silica, ethyl acetate/hexanes (1:2)] afforded a brown solid (124 mg, 89%). The analytical data were identical with those obtained for the product prepared from demetalation of Zn-2c.

5-(4-Formylphenyl)dipyrrin (2g) from demetalation of Zn-2g. A solution of Zn-2g (0.750 g, 1.34 mmol) in $CH_2Cl_2$ (134 mL) was treated with DTT (2.06 g, 13.4 mmol) at room temperature. After 1 h, the TLC examination of the reaction mixture indicated that the Zn-complex was completely consumed. The reaction mixture was diluted with $CH_2Cl_2$ and washed with water. The organic layer was dried ($Na_2SO_4$) and concentrated. Chromatography (silica, $CHCl_3$) afforded a dark oil (204 mg, 31%): $^1$H NMR δ 6.41 (dd, $J^1$=1.6 Hz, $J^2$=4.4 Hz, 2H), 6.52 (dd, $J^1$=0.4 Hz, $J^2$=4.0 Hz, 2H), 7.67-7.68 (m, 4H), 7.97-7.98 (m, 2H), 10.12 (s, 1H); $^{13}$C NMR δ 118.20, 128.45, 129.01, 131.40, 136.50, 139.94, 140.55, 143.46, 144.32, 191.82. Anal. Calcd for $C_{16}H_{12}N_2O$: C, 77.40; H, 4.87; N, 11.28. Found: C, 76.95; H, 4.94; N, 10.95; $\lambda_{abs}$ ($CH_2Cl_2$) 439 nm.

Synthesis of Porphyrins:

5,15-Dimesitylporphyrin (3). Following a published procedure (B. Littler, et al., *J. Org. Chem.*, 64, 2864-2872 (1999)), a solution of dipyrromethane (1e) (1.75 g, 12.0 mmol) and mesitaldehyde (1.78 g, 12.0 mmol) in $CHCl_3$ (1200 mL) was flushed with argon for 5 min and treated with $BF_3 \cdot OEt_2$ (840 μL, 3.3 mM) at room temperature for 30 min under argon. DDQ (4.09 g, 18.0 mmol) was added and the mixture was stirred for another 1 h. Triethylamine (920 μL, 3.3 mM) was added and the entire reaction mixture was filtered through a pad of alumina. The alumina pad was washed with $CHCl_3$ until the eluent was colorless. Removal of solvent and chromatography [silica, $CHCl_3$/hexanes, (2:1)] afforded a purple solid (922 mg, 28%): $^1$H NMR δ -3.08 (s, br, 2H), 1.84 (s, 12H), 2.66 (s, 6H), 7.32 (s, 4H), 8.88 (d, J=4.5 Hz, 4H), 9.32 (d, J=4.5 Hz, 4H), 10.22 (s, 2H); LD-MS obsd 544.9; FAB-MS obsd 546.2776, calcd 546.2783 ($C_{38}H_{34}N_4$); $\lambda_{abs}$ (toluene) 407, 502, 532, 576, 632 nm; $\lambda_{em}$ ($\lambda_{ex}$=500 nm, toluene) 632, 701 nm.

5-Bromo-10,20-dimesitylporphyrin (4). Following a known procedure (L. Nudy, et al., *Tetrahedron*, 40, 2359-2363 (1984); S. DiMagno, et al, *J. Org. Chem.*, 58, 5983-5993 (1993)), a solution of 3 (328 mg, 0.600 mmol) in $CHCl_3$ (200 mL) and pyridine (250 μL) was treated with NBS (106 mg, 0.600 mmol) at 0° C. After 25 min, the reaction was quenched with acetone (10 mL). Then the reaction mixture was washed with $H_2O$ and dried ($Na_2SO_4$). Chromatography [silica, $CHCl_3$/hexanes (1:2)] afforded three bands (in order of elution): the first band (purple) was dibrominated product (51 mg, 12%), the second band (purple) was the desired product, the third band (purple) was the starting material 3 (42 mg, 12%). The second band was re-chromatographed [silica, $CHCl_3$/hexanes (1:2)] affording a purple solid (274 mg, 73%). Data for the title compound: $^1$H NMR δ -2.87 (s, br, 2H), 1.83 (s, 12H), 2.65 (s, 6H), 7.31 (s, 4H), 8.78 (d, J=4.4 Hz, 4H), 9.22 (d, J=4.4 Hz, 2H), 9.66 (d, J=4.4 Hz, 2H), 10.08 (s, 1H); LD-MS obsd 624.7; FAB-MS obsd 624.1902, calcd 624.1889 ($C_{38}H_{33}BrN_4$); $\lambda_{abs}$ (toluene) 417, 511, 543, 589, 646 nm; $\lambda_{em}$, ($\lambda_{ex}$=515 nm) 647, 711 nm. Data for dibrominated porphyrin: $^1$H NMR δ -2.54 (s, br, 2H), 1.82 (s, 12H), 2.64 (s, 6H), 7.29 (s, 4H), 8.69 (d, J=4.4 Hz, 4H), 9.55 (d, J=4.4 Hz, 4H); LD-MS obsd 702.5, calcd 702.1 ($C_{38}H_{32}Br_2N_4Zn$).

5-Bromo-10,20-dimesitylporphinatozinc(II) (Zn-4). A solution of 4 (240 mg, 0.383 mmol) in $CHCl_3$ (50 mL) was treated overnight with $Zn(OAc)_2 \cdot 2H_2O$ (421 mg, 1.92 mmol, 5 eq) in methanol (2.0 mL) at room temperature. Standard workup gave a purple solid (259 mg, 98%): $^1$H NMR δ 1.81 (s, 12H), 2.66 (s, 6H), 7.31 (s, 4H), 8.87 (d, J=4.5 Hz, 4H), 9.30 (d, J=4.5 Hz, 2H), 9.74 (d, J=4.5 Hz, 2H), 10.14 (s, 1H); LD-MS obsd 688.0; FAB-MS obsd 686.1055, calcd 686.1024 ($C_{38}H_{31}BrN_4M$); $\lambda_{abs}$ (toluene) 420, 548, 583 nm; $\lambda_{em}$ ($\lambda_{ex}$=550 nm, toluene) 639 nm.

5,15-Dimesityl-10-(4,4,5,5-tetramethyl-1,3,2-dioxaborolan-2-yl)porphinatozinc (II) (Zn-5). Following a literature procedure (A. Hyslop, et al., *J. Am. Chem. Soc.*, 120, 12676-12677 (1998)), samples of Zn-4 (482 mg, 0.700 mmol), 4,4,5,5-tetramethyl-1,3,2-dioxaborolane (122 μL, 0.840 mmol), TEA (780 μL, 5.60 mmol) and $Pd(PPh_3)_2Cl_2$ (14.7 mg, 0.0210 mmol, 3% mol) were loaded into a 100 mL Schlenk flask under argon. Then 1,2-dichloroethane (35 mL) was added and the mixture was stirred at 85° C. TLC analysis [$CHCl_3$/hexanes (1:1)] after 1 h showed complete consumption of the starting porphyrin and the presence of a new, polar spot. The reaction mixture was cooled to room temperature, washed with water and dried ($Na_2SO_4$). Chromatography [silica, $CH_2Cl_2$/hexanes (1:1)] afforded a purple solid (479 mg, 93%): $^1$H NMR δ 1.80 (s, 12H), 1.85 (s, 12H), 2.66 (s, 6H), 7.30 (s, 4H), 8.90 (d, J=4.5 Hz, 2H), 8.96 (d, J=4.5 Hz, 2H), 9.36 (d, J=4.5 Hz, 2H), 9.87 (d, J=4.5 Hz, 2H), 10.24 (s, 1H); LD-MS obsd 735.9; FAB-MS obsd 734.2794, calcd 734.2771 ($C_{44}H_{43}N_4O_2Zn$); $\lambda_{abs}$ (toluene) 415, 543, 573 nm; $\lambda_{em}$ ($\lambda_{ex}$=540 nm, toluene) 581 637 nm.

Bis[5-[4-(5,15-dimesitylporphinatozinc(II)-10-yl)phenyl]dipyrrinato] palladium (II) (6). Following a standard method (P. Iovine, et al., *J. Am. Chem. Soc.*, 112, 8717-8727 (2000)), samples of Pd-2c (16 mg, 0.020 mmol), Zn-5 (29 mg, 0.040 mmol), $Ba(OH)_2 \cdot 8H_2O$ (13 mg, 0.040 mmol) and $Pd(PPh_3)_4$ (6.9 mg, 0.0060 mmol) were weighed into a 10 mL Schlenk flask. The flask was pump-purged with argon for three times. Dimethoxyethane (1.8 mL) and $H_2O$ (0.2 mL) were added under argon and the mixture was stirred at 80° C. TLC analysis (silica, $CHCl_3$) indicated complete consumption of the starting porphyrin after 2 h. The solvent was removed and the residue was chromatographed (silica, $CHCl_3$) affording a mixture of porphyrins. This mixture was purified by preparative SEC (THF) affording four major bands (in order of elution): (1) unidentified product ($t_R$=10.34 min); (2) desired triad ($t_R$=10.89 min); (3) mono-coupled byproduct ($t_R$=11.52 min, LD-MS obsd at m/z=1151, calcd 1153.0 ($C_{68}H_{52}N_8PdZn$); (4) monomeric porphyrin species ($t_R$=11.96 min). The second fraction from the SEC column was chromatographed (silica, $CHCl_3$), affording a red-purple solid (18 mg, 50%): $^1$H NMR δ 1.87 (s, 24H), 2.67 (s, 12H), 6.61-6.62 (m, 4H), 7.22-7.23 (m, 4H), 7.33 (s, 8H), 7.65 (s, 4H), 8.03 (d, J=8.0 Hz, 4H), 8.40 (d, J=8.0 Hz, 4H), 8.92 (d, J=4.4 Hz, 4H), 8.95 (d, J=4.4 Hz, 4H), 9.06 (d, J=4.4 Hz, 4H), 9.38 (d, J=4.4 Hz, 4H), 10.21 (s, 2H); LD-MS obsd 1758.6; calcd avg mass 1761.0 ($C_{106}H_{82}N_{12}PdZn_2$); $\lambda_{abs}$ (toluene, log ∈) 419 (5.72), 483 (4.88), 544 (4.70) nm; $\lambda_{em}$ ($\lambda_{ex}$=485 nm, toluene) 531 (w), 590, 637 nm.

5,15-Dimesityl-10-[4-(dipyrrin-5-yl)phenyl]porphinatozinc(II) (7a) by de-metalation of triad 6. A sample of triad 6 (14.5 mg, 8.23 μmol) in $CHCl_3$ (3.0 mL) was treated with DTT (13.0 mg, 82.3 μmol) at room temperature. UV-vis analysis indicated complete demetalation of the dipyrrin moiety (removal of palladium) after 2 h. The reaction mixture was washed with $H_2O$ and dried ($Na_2SO_4$). Chromatography [silica, $CHCl_3$→$CHCl_3$/MeOH (98:2)] afforded a purple solid (9.6 mg, 70%): $^1$H NMR δ 1.84 (s, 12H), 2.66 (s, 6H), 6.57 (d, J=3.6 Hz, 2H), 7.04 (d, J=3.6 Hz, 2H), 7.31 (s, 4H), 7.77 (s, 2H), 7.99 (d, J=8.0 Hz, 2H), 8.33 (d, J=8.0 Hz, 2H), 8.87 (d, J=4.4 Hz, 2H), 8.93 (d, J=4.4 Hz, 2H), 8.98 (d, J=4.4 Hz, 2H), 9.36 (d, J=4.4 HZ, 2H), 10.19 (s, 1H); LD-MS obsd 824.0; FAB-MS obsd 827.2864 (M$^+$+H); calcd 827.2841 ($C_{53}H_{42}N_6Zn_4$); $\lambda_{abs}$ (toluene) 417, 544 nm; $\lambda_{em}$ ($\lambda_{ex}$=540 nm, toluene) 590, 637 nm.

5,15-Dimesityl-10-[4-(dipyrrin-5-yl)phenyl]porphinatozinc(II) (7a) via oxidation of 9a. A mixture of 9a (49 mg, 0.064 mmol) and Zn(OAc)$_2$.2H$_2$O (70 mg, 0.32 mmol, 5 eq) in THF (5 mL) was treated with p-chloranil (16 mg, 0.064 mmol) at room temperature. The mixture was stirred overnight. The standard workup and chromatography [silica, CH$_2$Cl$_2$/MeOH (99:1)] afforded a purple solid (38 mg, 72%). The characterization data were identical with those obtained for the product prepared from triad 6.

5,15-Bis(3,5-di-tert-butylphenyl)-10-mesityl-20-[4-(dipyrrin-5-yl)phenyl]porphinatozinc(II) (7b). A mixture of 9b (41 mg, 0.040 mmol) and Zn(OAc)$_2$.2H$_2$O (44 mg, 0.20 mmol, 5 eq) in THF (3 mL) was treated with p-chloranil (9.8 mg, 0.040 mmol) overnight at room temperature. The standard workup and chromatography [silica, CH$_2$Cl$_2$/MeOH (99:1)] afforded a purple solid (31 mg, 71%): $^1$H NMR δ 1.54 (s, 36H), 1.87 (s, 6H), 2.63 (s, 3H), 6.55-6.57 (m, 2H), 7.04-7.05 (m, 2H), 7.29 (s, 2H), 7.76 (s, 2H), 7.80-7.81 (m, 2H), 7.89 (d, J=8.1 Hz, 2H), 8.13-8.14 (m, 4H), 8.34 (d, J=8.1 Hz, 2H), 8.81 (d, J=4.5 Hz, 2H), 8.97-9.05 (m, 6H); LD-MS obsd 1085.8; FAB-MS obsd 1085.5175 (M$^+$+H); calcd 1085.5188 (C$_{72}$H$_{72}$N$_6$Zn); $\lambda_{abs}$ (toluene) 425, 551, 590 nm; $\lambda_{em}$ ($\lambda_{ex}$=550 nm, toluene) 599, 648 nm.

5,15-Bis(4-methylphenyl)-10-[4-(dipyrrin-5-yl)phenyl]-20-phenylporphyrin (7c). Following a standard procedure (G. Geier, III, et al., *J. Porphyrins Phthalocyanines*, 5, 810-823 (2001)), a sample of diacyldipyrromethane 11a (137 mg, 0.300 mmol) in THF/methanol (16 mL, 3:1) was treated with NaBH$_4$ (570 mg, 15.0 mmol). After 40 min (TLC showed reaction completion), the reaction was quenched with aqueous NH$_4$Cl. The mixture was extracted with CH$_2$Cl$_2$. The combined extracts were washed with water, dried (Na$_2$SO$_4$) and concentrated. The resulting dicarbinol 11a-diol and compound 10 (109 mg, 0.300 mmol) were dissolved in CH$_2$Cl$_2$ (120 mL) and treated with InCl$_3$ (8.4 mg, 0.038 mmol, 0.32 mM). The reaction mixture was stirred at room temperature for 20 min, then DDQ (204 mg, 0.900 mmol) was added and the mixture was stirred for 1 h at room temperature. The mixture was filtered through a pad of silica [eluted with a mixture of CH$_2$Cl$_2$/methanol (95:5)] and the filtrate was concentrated. Chromatography [silica, CH$_2$Cl$_2$/methanol (98:2)] afforded a purple solid (38 mg, 16%): $^1$H NMR δ -2.73 (s, 2H), 2.72 (s, 6H), 6.59 (dd, J$^1$=0.8 Hz, J$^2$=4.0 Hz, 2H), 7.06 (d, J=3.6 Hz, 2H), 7.57 (d, J=8.0 Hz, 4H), 7.65-7.82 (m, 5H), 7.91 (d, J=7.6 Hz, 2H), 8.12 (d, J=7.6 Hz, 4H), 8.23 (dd, J$^1$=1.6 Hz, J$^2$=7.2 Hz, 2H), 8.32 (d, J=7.6 Hz, 2H), 8.80-9.00 (m, 8H); LD-MS obsd 784.6; FAB-MS obsd 785.3379 (M$^+$+H), calcd 785.3393 (C$_{55}$H$_{40}$N$_6$); $\lambda_{abs}$ (toluene) 421, 516, 551, 593, 648 nm; $\lambda_{em}$, ($\lambda_{ex}$=550 nm, toluene) 652, 720 nm.

5,15-Bis(4-methoxyphenyl)-10-[4-(dipyrrin-5-yl)phenyl]-20-phenylporphyrin (7d). Following a standard procedure (G. Geier, III, et al., *J. Porphyrins Phthalocyanines*, 5, 810-823 (2001)), a sample of diacyldipyrromethane 11b (147 mg, 0.300 mmol) in THF/methanol (16 mL, 10:1) was treated with NaBH$_4$ (228 mg, 6.00 mmol). After 40 min (TLC showed reaction completion), the reaction was quenched by with aqueous NH$_4$Cl. The mixture was extracted with CH$_2$Cl$_2$. The combined extracts were washed with water, dried (Na$_2$SO$_4$) and concentrated. The resulting dicarbinol 11b-diol and compound 10 (109 mg, 0.300 mmol) were dissolved in CH$_2$Cl$_2$ (120 mL) and treated with InCl$_3$ (8.4 mg, 0.038 mmol, 0.32 mM). The reaction mixture was stirred at room temperature for 20 min, then DDQ (204 mg, 0.900 mmol) was added and the mixture was stirred for 1 h. The mixture was filtered through a pad of silica [eluted with a mixture of CH$_2$Cl$_2$/methanol (95:5)] and the filtrate was concentrated. Chromatography [silica, CH$_2$Cl$_2$/methanol (98:2)] afforded a purple solid (23 mg, 10%): $^1$H NMR δ -2.72 (s, 2H), 4.11 (s, 6H), 6.60 (d, J=3.6 Hz, 2H), 7.06 (d, J=4.0 Hz, 2H), 7.31 (d, J=8.4 Hz, 4H), 7.72-7.83 (m, 5H), 7.91 (d, J=8.4 Hz, 2H), 8.15 (d, J=8.0 Hz, 4H), 8.23 (dd, J$^1$=2.0 Hz, J$^2$=7.6 Hz, 2H), 8.33 (d, J=7.6 Hz, 2H), 8.82-8.98 (m, 8H); LD-MS obsd 815.7; FAB-MS obsd 817.3304 (M$^+$+H), calcd 817.3291 (C$_{55}$H$_{40}$N$_6$O$_2$); $\lambda_{abs}$ (toluene) 422, 517, 553, 593, 650 nm; $\lambda_{em}$ ($\lambda_{ex}$=550 nm, toluene) 656, 723 nm.

5-15-Dimesityl-10-(4-formylphenyl)porphyrin (8a). Following a standard procedure for Suzuki coupling (L. Yu and J. Lindsey, *Tetrahedron*, 57, 9285-9298 (2001)), samples of Zn-4 (2.05 g, 3.28 mmol), 4-formylphenyl boronic acid (984 mg, 6.56 mmol), anhydrous K$_2$CO$_3$ (3.62 g, 26.2 mmol) and Pd(PPh$_3$)$_4$ (381 mg, 0.330 mmol, 10 mol %) were weighed into a Schlenk flask. The flask was pump-purged with argon three times. Toluene/DMF (164 mL, 1:1) was added and the mixture was heated to 85° C. under argon. TLC analysis (silica, CHCl$_3$) after 5 h indicated complete consumption of the starting porphyrin and the formation of a new polar spot. Removal of the solvent and chromatography (silica, CHCl$_3$) afforded a purple solid (1.94 g, 91%): $^1$H NMR δ -2.90 (s, br, 2H), 1.84 (s, 12H), 2.64 (s, 6H), 7.30 (s, 4H), 8.27 (d, J=8.0 Hz, 2H), 8.41 (d, J=8.1 Hz, 2H), 8.74-8.77 (m, 4H), 8.84 (d, J=4.8 Hz, 2H), 9.29 (d, J=4.8 Hz, 2H), 10.16 (s, 1H), 10.38 (s, 1H); LD-Ms obsd 649.7, FAB-MS obsd 650.3058, calcd 650.3046 (C$_{45}$H$_{38}$N$_4$O); $\lambda_{abs}$ (toluene) 415, 509, 540, 584, 640 nm; $\lambda_{em}$ ($\lambda_{ex}$ n=510 nm, toluene) 642, 709 nm.

5-15-Dimesityl-10-[4-(dipyrromethan-5-yl)phenyl]porphyrin (9a). A mixture of 8a (65 mg, 0.10 mmol) and pyrrole (2.7 g, 40 mmol) in CH$_2$Cl$_2$ (5.0 mL) was treated with TFA (9.6 µL, 0.11 mmol) for 2 h at room temperature. The reaction mixture was neutralized with TEA. The solvent and the excess pyrrole were removed under reduced pressure. Chromatography [silica, CHCl$_3$/TEA (99:1)] afforded a purple solid (66 mg, 86%): $^1$H NMR δ -2.90 (s, br, 2H), 1.84 (s, 12H), 2.65 (s, 6H), 5.83 (s, 1H), 6.18-6.19 (m, 2H), 6.30-6.31 (m, 2H), 6.86-6.87 (m, 2H), 7.30 (s, 4H), 7.59 (d, J=8.4 Hz, 2H), 8.17 (d, J=8.4 Hz, 2H), 8.22 (s, br, 2H), 8.73 (d, J=4.4 Hz, 2H), 8.82-8.84 (m, 4H), 9.27 (d, J=4.4 Hz, 2H), 10.11 (s, 1H); LD-MS obsd 765.3, FAB-MS obsd 767.3866, calcd 767.3862 (C$_{53}$H$_{46}$N$_6$); $\lambda_{abs}$ (toluene) 414, 508, 584, 640 nm; $\lambda_{em}$ ($\lambda_{ex}$=510 nm, toluene) 642, 710 nm.

5,15-Bis(3,5-di-tert-butylphenyl)-10-[4-(dipyrromethan-5-yl)phenyl]-20-mesitylporphyrin (9b). A solution of 8b (227 mg, 0.250 mmol) and pyrrole (5.0 g, 75 mmol) in CH$_2$Cl$_2$ (12 mL) was treated with TFA (22 µL, 0.28 mmol, 1.1 eq) at room temperature. TLC analysis [silica, CHCl$_3$/TEA (99:1)] showed complete consumption of the starting porphyrin-benzaldehyde after 2 h. The reaction mixture was neutralized with TEA. The solvent and the excess pyrrole were removed under reduced pressure. Chromatography [silica, CHCl$_3$/TEA (99:1)] afforded the desired product as a purple solid (205 mg, 80%): $^1$H NMR δ -2.65 (br s, 2H), 1.53 (s, 36H), 1.86 (s, 6H), 2.62 (s, 3H), 5.84 (s, 1H), 6.18 (br s, 2H), 6.29-6.32 (m, 2H), 6.85-6.87 (m, 2H), 7.27 (s, 2H), 7.60 (d, J=8.1 Hz, 2H), 7.78-7.79 (m, 2H), 8.08-8.09 (m, 4H), 8.18 (d, J=8.1 Hz, 2H), 8.22 (br s, 2H), 8.69 (d, J=4.8 Hz, 2H), 8.83-8.88 (m, 6H); LD-MS obsd 1024.8; FAB-MS obsd 1024.6115, calcd 1024.6131 (C$_{72}$H$_{76}$N$_6$); $\lambda_{abs}$ (toluene) 421, 516, 550, 593, 649 nm; $\lambda_{em}$ ($\lambda_{ex}$=515 nm, toluene) 652, 720 nm.

5-[4-(Dipyrrin-5-yl)phenyl]dipyrromethane (10). Following a standard procedure with slight modification (R. Loewe, et al., *J. Mater. Chem.*, 12, 3438-3451 (2002); M. Speckbacher, et al., *Inorg. Chem.*, in press (2003)), a sample of 2g (0.320 g, 1.30 mmol) in CH$_2$Cl$_2$ (4.6 mL) was mixed thoroughly with pyrrole (4.60 mL, 65.0 mmol). The mixture was treated with TFA (0.120 ml, 0.156 mmol). The reaction mixture was stirred at room temperature for 5 min and quenched with 0.1 N aqueous NaOH. The reaction mixture was extracted with ethyl acetate, dried ($Na_2SO_4$) and concentrated. The dark residue obtained was chromatographed [silica, hexanes/ethyl acetate (3:1)] to give dark oil. The dark oil was dissolved in 9:1 hexanes/ethyl acetate and the precipitate that formed was filtered off. The yellow filtrate was concentrated to afford an orange solid (196 mg, 41%): mp 129-130° C.; $^1$H NMR δ 5.57 (s, 1H), 5.96 (s, 2H), 6.20-6.21 (m, 2H), 6.40 (dd, $J^1$=4.0 Hz, $J^2$=1.2 Hz, 2H), 6.63 (d, J=4.0 Hz, 2H), 6.75-6.76 (m, 2H), 7.29 (d, J=8.0 Hz, 2H), 7.46 (d, J=8.0 Hz, 2H), 7.64 (s, 2H), 8.02 (s, 2H). (In addition, signals consistent with that for the N-confused dipyrromethane were present in the $^1$H NMR spectrum, indicating a 96:4 ratio of 10:N-confused isomer. All data reported here were derived from this mixture.) $^{13}$C NMR δ 43.92, 107.53, 108.63, 117.60, 117.68, 127.71, 129.01, 130.14, 131.27, 132.20, 143.69; FAB-MS obsd 365.1779 ($M^+$+H), calcd 365.1766 ($C_{24}H_{20}N_4$); $\lambda_{abs}$ 431 nm.

Bis[5-[4-(5,15-dimesitylporphinatozinc(II)-10-yl)phenyl]dipyrrinato]zinc(II) (12a). A solution of 7a (9.60 mg, 0.0116 mmol) in $CHCl_3$ (3 mL) was treated overnight with Zn$(OAc)_2 \cdot 2H_2O$ (12.7 mg, 0.0579 mmol) in methanol (0.2 mL) at room temperature. UV-vis analysis showed complete metalation. The reaction mixture was washed with aqueous $NaHCO_3$ and $H_2O$. The organic layer was dried ($Na_2SO_4$) and concentrated, affording a purple solid (9.7 mg, 97%): $^1$H NMR ($CDCl_3$) δ 1.87 (s, 24H), 2.67 (s, 12H), 6.66 (d, J=4.4 Hz, 4H), 7.23 (d, J=4.4 Hz, 4H), 7.33 (s, 8H), 7.78 (s, 4H), 8.01 (d, J=7.6 Hz, 4H), 8.39 (d, J=7.6 Hz, 4H), 8.92 (d, J=4.4 Hz, 4H), 8.95 (d, J=4.4 Hz, 4H), 9.06 (d, J=4.4 Hz, 4H), 9.38 (d, J=4.4 Hz, 4H), 10.21 (s, 2H); LD-MS obsd 1720.1; calcd avg mass 1720.4 ($C_{106}H_{82}N_{12}Zn_3$); $\lambda_{abs}$ (toluene, log ∈) 419 (5.72), 486 (4.93), 544 (4.58) nm; $\lambda_{em}$ ($\lambda_{ex}$=485 nm, toluene) 531 (w), 590, 637 nm.

Bis[5-[4-[5,15-bis(3,5-di-tert-butylphenyl)-10-mesitylporphinatozinc(II)-20-yl]phenyl]dipyrrinato]zinc(II) (12b). A solution of 7b (31 mg, 0.028 mmol) in $CHCl_3$ (3 mL) was treated overnight with a solution of Zn$(OAc)_2 \cdot 2H_2O$ (22 mg, 0.10 mmol) in MeOH (0.5 mL) at room temperature. The standard workup and washing with methanol (sonication and filtration) afforded a purple solid (28 mg, 87%): $^1$H NMR δ 1.49 (s, 72H), 1.81 (s, 12H), 2.57 (s, 6H), 6.58-6.60 (m, 4H), 7.16-7.17 (m, 4H), 7.22 (s, 4H), 7.72-7.74 (m, 8H), 7.94 (d, J=7.8 Hz, 4H), 8.03-8.08 (m, 8H), 8.31 (d, J=7.8 Hz, 4H), 8.73-8.76 (m, 4H), 8.86-8.95 (m, 6H), 9.01-9.02 (m, 6H); LD-MS obsd 2238.2; calcd avg mass 2236.9 ($C_{144}H_{142}N_{12}Zn_3$); $\lambda_{abs}$ (toluene, log ∈) 423 (5.85), 486 (4.97), 551 (4.68), 590 (4.04) nm; $\lambda_{em}$ ($\lambda_{ex}$=485 nm, toluene) 597, 647 nm.

Bis{5-[4-[5,15-bis(4-methylphenyl)-10-phenylporphinatozinc(II)-20-yl]phenyl]dipyrrinato}zinc(II) (12c). A solution of 7c (24 mg, 0.030 mmol) in $CHCl_3$ (3 mL) was treated overnight with a solution of Zn$(OAc_2 \cdot 2H_2O$ (49 mg, 0.23 mmol) in MeOH (0.5 mL) at room temperature. The standard workup afforded a purple solid. The solid was washed with methanol, affording a purple solid (22 mg, 83%): $^1$H NMR δ 2.74 (s, 12H), 6.68 (d, J=4.8 Hz, 4H), 7.25 (d, J=4.4 Hz, 4H), 7.59 (d, J=7.6 Hz, 8H), 7.72-7.84 (m, 10H), 8.03 (d, J=8.0 Hz, 4H), 8.15 (d, J=8.4 Hz, 8H), 8.24-8.25 (m, 4H), 8.38 (d, J=8.0 Hz, 4H), 8.92-9.14 (m, 16H); LD-MS obsd 1755.3; calcd 1754.4 ($C_{110}H_{74}N_{12}Zn_3$); $\lambda_{abs}$ (toluene) 427, 486, 557, 597 nm; $\lambda_{em}$ ($\lambda_{ex}$=485 nm, toluene) 599, 648 nm.

Bis{5-[4-[5,15-bis(4-methoxyphenyl)-10-phenylporphinatozinc(II)-20-yl]phenyl]dipyrrinato}zinc(II) (12d). A solution of 7d (15 mg, 0.018 mmol) in $CHCl_3$ (2 mL) was treated overnight with a solution of Zn$(OAc)_2 \cdot 2H_2O$ (30.0 mg, 0.135 mmol) in MeOH (0.5 mL) at room temperature. The standard workup afforded a purple solid. The solid was washed with methanol, affording a purple solid (14 mg, 85%): $^1$H NMR δ 4.12 (s, 12H), 6.68 (d, J=4.0 Hz, 4H), 7.22-7.38 (m, 12H), 7.72-7.84 (m, 10H), 8.03 (d, J=8.0 Hz, 4H), 8.17 (d, J=8.0 Hz, 8H), 8.25 (d, J=7.2 Hz, 4H), 8.38 (d, J=7.6 Hz, 4H), 8.97 (d, J=4.0 Hz, 4H), 9.03 (d, J=4.4 Hz, 4H), 9.09-9.10 (m, 8H); LD-MS obsd 1820.3; calcd 1818.4 ($C_{110}H_{74}N_{12}O_4Zn_3$); $\lambda_{abs}$ (toluene) 426, 486, 551, 591 nm; $\lambda_{em}$ ($\lambda_{ex}$=485 nm, toluene) 600, 650 nm.

5,15-Bis[4-(dipyrrin-5-yl)phenyl]-10,20-dimesitylporphyrin (13). Following a general procedure (B. Littler, et al., J. Org. Chem., 64, 2864-2872 (1999)), a solution of 1 h (132 mg, 0.500 mmol) and 2g (124 mg, 0.500 mmol) in $CH_2Cl_2$ (50 mL) was treated with TFA (69 μL, 89 μmol). The reaction mixture was stirred at room temperature and monitored by UV-vis spectroscopy. After 60 min, DDQ (170 mg, 0.75 mmol) was added and the reaction mixture was stirred at room temperature for 1 h. Triethylamine (0.1 mL) was added and the mixture was concentrated. Chromatography [silica, $CHCl_3$/ethyl acetate (3/1)] afforded a purple solid (34 mg, 14%): $^1$H NMR δ −2.56 (brs, 2H), 1.87 (s, 12H), 2.65 (s, 6H), 6.59 (d, J=3.6 Hz, 4H), 7.04 (d, J=3.6 Hz, 4H), 7.31 (s, 4H), 7.81 (s, 4H), 7.91 (d, J=8.0 Hz, 4H), 8.34 (d, J=8.0 Hz, 4H), 8.78 (d, J=4.8 Hz, 4H), 8.89 (d, J=4.8 Hz, 4H); LD-MS obsd 981.96; FAB-MS obsd 983.4590 [M+H]$^+$, calcd 983.4550 ($C_{68}H_{54}N_8$+H); $\lambda_{abs}$ 421, 516, 551, 592, 649 nm.

5,15-Bis[4-(methoxycarbonyl)phenyl]-10,20-dimesitylporphyrin (14). Following a general procedure (B. Littler, et al., J. Org. Chem., 64, 2864-2872 (1999)), a solution of 1 h (1.32 g, 5.00 mmol) and methyl 4-formylbenzoate (0.821 g, 5.00 mmol) in $CH_2Cl_2$ (500 mL) was treated with TFA (690 μL, 890 μmol). The reaction mixture was stirred at room temperature and monitored by UV-vis spectroscopy. After 30 min, DDQ (1.70 g, 7.50 mmol) was added and the reaction mixture was stirred at room temperature for 1 h. Triethylamine (1 mL) was added and the mixture was poured on to a pad of alumina and eluted with $CH_2Cl_2$ until the eluent was pale brown. The solvent was removed under vacuum. The resulting dark residue was dissolved in toluene (100 mL) and heated under reflux for 1 h in the presence of DDQ (1.14 g, 5.00 mmol) to oxidize any remaining chlorin. After cooling to room temperature, the reaction mixture was passed through a pad of alumina and eluted with $CH_2Cl_2$. The solvent was removed under vacuum. Chromatography (silica, $CH_2Cl_2$) gave a purple solid (360 mg, 18%): $^1$H NMR δ −2.63 (s, 2H), 1.84 (s, 12H), 2.63 (s, 6H), 4.11 (s, 6H), 7.28 (s, 4H), 8.31 (d, J=8.4 Hz, 4H), 8.43 (d, J=8.4 Hz, 4H), 8.72 (d, J=4.4 Hz, 4H), 8.75 (d, J=4.4 Hz, 4H); LD-MS obsd 814.61, calcd 814.3519 ($C_{54}H_{46}N_4O_4$); $\lambda_{abs}$ 420, 515, 549, 594, 648 nm.

5,15-Bis[4-(hydroxymethyl)phenyl]-10,20-dimesitylporphyrin (15). A solution of 14 (407 mg, 0.500 mmol) in anhydrous THF (50 mL) was treated with $LiAlH_4$ (76 mg, 2.0 mmol). The reaction mixture was stirred at room temperature. After 15 min, the reaction was quenched with methanol and concentrated. The dark residue was suspended in $CHCl_3$ and poured on to a pad of alumina. The alumina pad was eluted with $CHCl_3$/methanol (4:1) until the eluant was colorless. The solvent was evaporated under vacuum. Chromatography [silica, $CHCl_3$/methanol (4:1)] afforded a purple solid (340 mg, 89%): $^1$H NMR δ −2.63 (s, 2H), 1.84 (s, 12H), 2.63 (s, 6H), 5.07 (s, 4H), 7.28 (s, 4H), 7.75 (d, J=8.0 Hz, 4H), 8.22 (d, J=8.0 Hz, 4H), 8.69 (d, J=4.8 Hz, 4H), 8.80 (d, J=4.4 Hz, 4H); LD-MS obsd 758.54, calcd 758.3621 ($C_{52}H_{46}N_4O_2$); $\lambda_{abs}$ 419, 515, 549, 593, 647 nm.

5,15-Bis(4-formylphenyl)-10,20-dimesitylporphyrin (16). A solution of 15 (0.190 g, 0.250 mmol) in $CH_2Cl_2$ (25 mL) was treated with pyridinium chlorochromate (216 mg, 1.00 mmol). The reaction mixture was stirred at room temperature and monitored by TLC. After 90 min, the reaction mixture was poured on to a silica column (poured in $CHCl_3$) and eluted with $CHCl_3$/methanol (95:5) affording a purple solid (156 mg, 83%): $^1$H NMR δ −2.63 (brs, 2H), 1.84 (s, 12H), 2.63 (s, 6H), 7.29 (s, 4H), 8.28 (d, J=8.4 Hz, 4H), 8.41 (d, J=8.4 Hz, 4H), 8.71-8.78 (m, 8H), 10.39 (s, 2H); LD-MS obsd 755.24, calcd 754.3308 ($C_{52}H_{42}N_4O_2$); $\lambda_{abs}$ 422, 515, 549, 594, 649 nm.

5,15-Bis[4-(dipyrromethan-5-yl)phenyl]-10,20-dimesitylporphyrin(17). Following a general procedure (B. Littler, et al., *J. Org. Chem.*, 64, 1391-1396 (1999)) with slight modification, a mixture of 16 (0.130 g, 0.172 mmol) and pyrrole (0.600 ml, 8.60 mmol) in $CH_2Cl_2$ (3.5 mL) was treated with TFA (29 μL, 0.38 mmol) under argon. After 20 min, the reaction mixture was quenched with 0.1 M aqueous NaOH. The reaction mixture was extracted with $CHCl_3$. The organic layer was washed with water, dried ($Na_2SO_4$) and concentrated. Chromatography (silica, $CHCl_3$) followed by trituration with methanol afforded a dark solid (122 mg, 72%): $^1$H NMR δ −2.58 (s, 2H), 1.86 (s, 12H), 2.65 (s, 6H), 5.82 (s, 1H), 6.19 (s, 2H), 6.31 (m, 2H), 6.86 (m, 2H), 7.29 (s, 4H), 7.61 (d, J=8.0 Hz, 4H), 8.20 (d, J=4.4 Hz, 4H), 8.23 (s, 4H), 8.73 (d, J=4.8 Hz, 4H), 8.85 (d, J=4.8 Hz, 4H); LD-MS obsd 986.81, calcd 986.4784 ($C_{68}H_{58}N_8$); $\lambda_{abs}$ 421, 515, 549, 594, 649 nm.

5,15-Bis[4-(dipyrrin-5-yl)phenyl]-10,20-dimesitylporphyrin (13) from 17. A solution of 17 (114 mg, 0.115 mmol) in THF (5 mL) was treated with DDQ (55 mg, 0.24 mmol). The reaction mixture was stirred at room temperature for 30 min. Then, the mixture was poured on to a pad of silica (poured in $CH_2Cl_2$) and eluted with $CH_2Cl_2$/methanol (90:10). The solvent was evaporated under vacuum to afford a dark solid. The dark solid was washed with methanol affording a purple solid (26 mg, 23%): The data were consistent with that of the data reported for the condensation of 5-mesityldipyrromethane (1h) and dipyrrin-benzaldehyde 2g.

The foregoing is illustrative of the present invention, and is not to be construed as limiting thereof. The invention is defined by the following claims, with equivalents of the claims to be included therein.

That which is claimed is:

1. A method of synthesizing a dipyrrin-substituted porphyrinic macrocycle, comprising:
    condensing a dipyrromethane-dicarbinol with a dipyrrin-substituted dipyrromethane in a weakly polar solvent in the presence of a Lewis acid to produce a dipyrrin-substituted porphyrinic macrocycle.

2. A method according to claim 1, wherein said dipyrromethane-dicarbinol has at least one porphyrinic macrocycle covalently coupled thereto.

3. The method according to claim 2, wherein said porphyrinic macrocycle compound is metalated.

4. The method according to claim 3, wherein said condensing step is carried out without demetalation of said porphyrinic macrocycle.

5. The method according to claim 1, wherein said solvent has a dielectric constant of about 20 or less at room temperature.

6. The method according to claim 1, wherein said solvent is selected from the group consisting of hydrocarbons, chlorinated hydrocarbons, ethers, esters, glymes, tributyl borate, carbon disulfide, and mixtures thereof.

7. The method according to claim 1, wherein said Lewis acid is selected from the group consisting of CsCl, $SmCl_3.6H_2O$, $InCl_3$, $CrF_3$, $AlF_3$, $Sc(OTf)_3$, $TiF_4$, $BEt_3$, $GeI_4$, $EuCl_3.nH_2O$, $LaCl_3$, and $Ln(OTf)_3$ where Ln =lanthanide.

* * * * *

UNITED STATES PATENT AND TRADEMARK OFFICE
CERTIFICATE OF CORRECTION

PATENT NO.       : 7,947,828 B2  
APPLICATION NO.  : 12/756563  
DATED            : May 24, 2011  
INVENTOR(S)      : Yu et al.

Page 1 of 4

It is certified that error appears in the above-identified patent and that said Letters Patent is hereby corrected as shown below:

In the Patent:
Column 1, Line 9: Please correct "now U.S. Pat. No. 7,723,513 allowed"
  to read -- U.S. Pat. No. 7,723,513 now allowed --
  Line 13: Please add heading to read -- GOVERNMENT FUNDING --
Column 7, Line 18: Please correct "$\in_{\lambda max}$" to read -- $\varepsilon_{\lambda max}$ --

Column 15, Scheme 5, line 4-8, figure 1e: Please correct

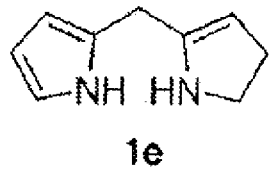

to read:

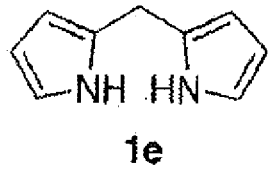

Signed and Sealed this  
Twenty-second Day of November, 2011

David J. Kappos  
*Director of the United States Patent and Trademark Office*

Column 17, lines 4-20, Figure Zn-5: Please correct
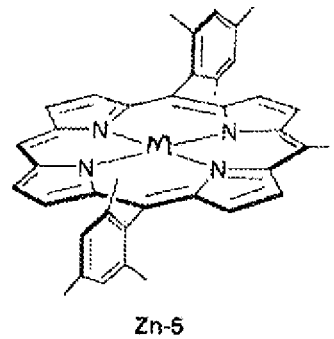
Zn-5
to read:
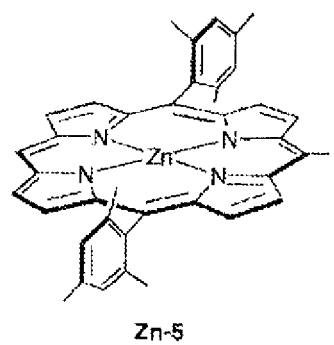
Zn-5
Column 22, Scheme 9, lines 25-38, last figure: Please correct
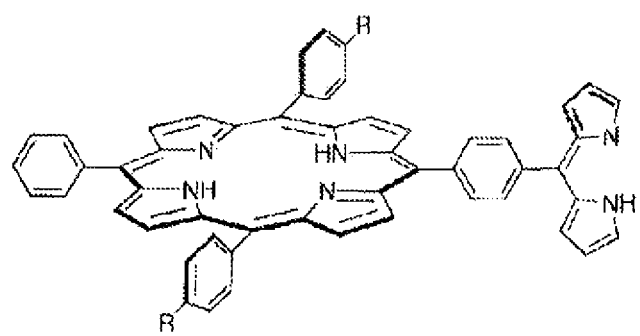
to read:
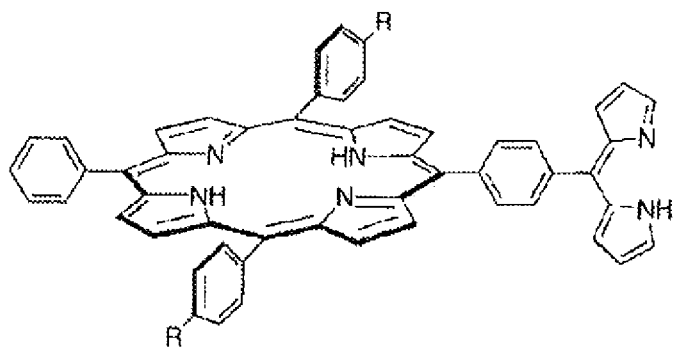

CERTIFICATE OF CORRECTION (continued)
U.S. Pat. No. 7,947,828 B2

Page 3 of 4

Column 26, Scheme 11, lines 49-65, last figure: Please correct

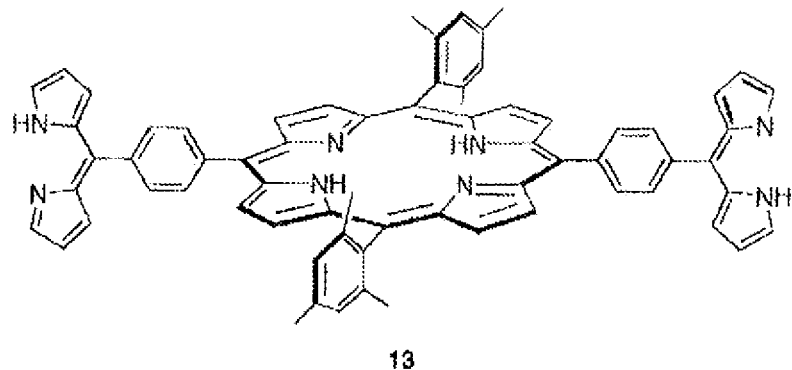

13 to read:

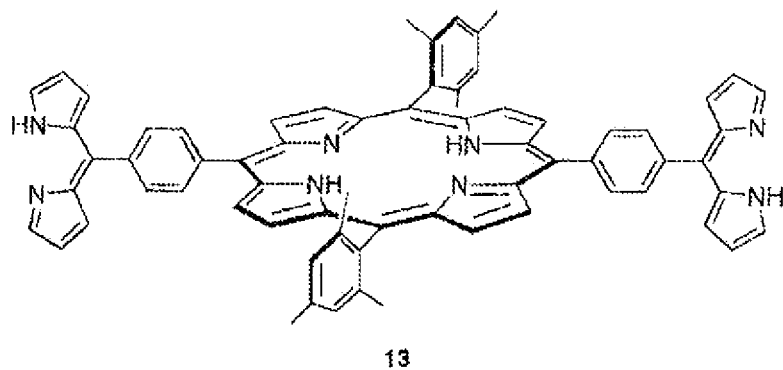

13

Column 30, Scheme 12, lines 1-17, next to last figure: Please correct

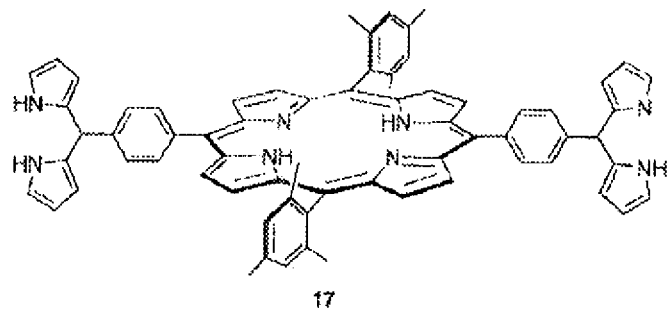

17 to read:

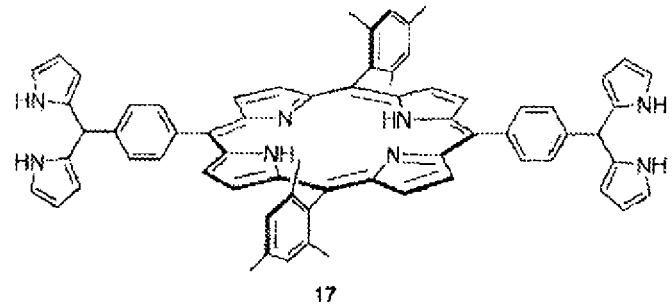

17

CERTIFICATE OF CORRECTION (continued)
U.S. Pat. No. 7,947,828 B2

Column 32, Line 16: Please correct "log $\in$" to read -- log $\varepsilon$ --
        Line 30: Please correct "log $\in$" to read -- log $\varepsilon$ --
Column 33, Line 18: Please correct "2, $\lambda_2$" to read -- $\lambda_{abs}$ -- and
        correct "log $\in$" to read -- log $\varepsilon$ --
        Line 34: Please correct "log $\in$" to read -- log $\varepsilon$ --

Line 47: Please correct "$\in$" to read -- $\varepsilon$ --

Column 34, Line 25: Please correct "log $\in$" to read -- log $\varepsilon$ --
        Line 48: Please correct "log $\in$" to read -- log $\varepsilon$ --

Column 35, Line 2: Please correct "log $\in$" to read -- log $\varepsilon$ --
        Line 20: Please correct "$\in$" to read -- $\varepsilon$ --

Column 36, Line 57: Please correct "$\in$" to read -- $\varepsilon$ --

Column 38, Line 50: Please correct "$\in$" to read -- $\varepsilon$ --

Column 41, Line 50: Please correct "$\in$" to read -- $\varepsilon$ --
        Line 50: Please correct "$\in$" to read -- $\varepsilon$ --